(12) United States Patent
Della Ciana et al.

(10) Patent No.: US 11,179,481 B2
(45) Date of Patent: *Nov. 23, 2021

(54) TRICARBOCYANINE-CYCLODEXTRIN(S) CONJUGATES AND USE THEREOF

(71) Applicant: CYANAGEN S.R.L., Bologna (IT)

(72) Inventors: Leopoldo Della Ciana, Bologna (IT); Norbert Gretz, Mannheim (DE); Rossana Perciaccante, Granarolo dell'Emilia (IT); Federica Rodeghiero, Granarolo dell'Emilia (IT); Stefania Geraci, Heidelberg (DE); Jiaguo Huang, Mannheim (DE); Zeneida Herrera Pérez, Mannheim (DE); Johannes Pill, Leimen (DE); Stefanie Weinfurter, Hattersheim (DE)

(73) Assignee: CYANAGEN S.R.L., Bologna (IT)

( * ) Notice: Subject to any disclaimer, the term of this patent is extended or adjusted under 35 U.S.C. 154(b) by 63 days.

This patent is subject to a terminal disclaimer.

(21) Appl. No.: 16/557,162

(22) Filed: Aug. 30, 2019

(65) Prior Publication Data

US 2019/0381196 A1  Dec. 19, 2019

Related U.S. Application Data

(62) Division of application No. 14/713,459, filed on May 15, 2015, now Pat. No. 10,441,666.

(30) Foreign Application Priority Data

May 16, 2014 (IT) .......................... TO2014A000391

(51) Int. Cl.
*A61K 49/00* (2006.01)
*A61M 36/14* (2006.01)
*C09B 69/10* (2006.01)
*C08B 37/16* (2006.01)
*C08L 5/16* (2006.01)

(52) U.S. Cl.
CPC ...... *A61K 49/0032* (2013.01); *A61K 49/0004* (2013.01); *A61K 49/0054* (2013.01); *C08B 37/0012* (2013.01); *C08L 5/16* (2013.01); *C09B 69/105* (2013.01); *A61K 49/0017* (2013.01)

(58) Field of Classification Search
None
See application file for complete search history.

(56) References Cited

U.S. PATENT DOCUMENTS 10,441,666 B2 * 10/2019 Della Ciana ....... A61K 49/0004

\* cited by examiner

*Primary Examiner* — Michael G. Hartley
*Assistant Examiner* — Melissa J Perreira
(74) *Attorney, Agent, or Firm* — Nixon & Vanderhye P.C.

(57) ABSTRACT

The present invention relates to novel tricarbocyanine-cyclodextrin(s) conjugates useful as markers in the diagnosis of kidney diseases, a diagnostic composition comprising said conjugates, their use and their production.

13 Claims, 5 Drawing Sheets

TRICARBOCYANINE-CYCLODEXTRIN(S) CONJUGATES AND USE THEREOF

CROSS-REFERENCES TO RELATED APPLICATIONS

This application is a divisional of application Ser. No. 14/713,459 filed May 15, 2015, which claims priority to IT Patent Application No. TO2014A000391 filed May 16, 2014, the entire contents of which is hereby incorporated by reference in this application.

FIELD OF THE INVENTION

The present invention relates to novel tricarbocyanine-cyclodextrin(s) conjugates, and use thereof as diagnostic agents for kidney diseases.

BACKGROUND OF THE INVENTION

Fructans are used as markers in kidney diagnostics and in particular to determine the glomerular filtration rate (GFR) as a test for kidney function.

Fructans are straight or branched chain oligosaccharides and polysaccharides with an sucrose terminal end. Fructans can have different physical properties, such as water solubility depending on the degree of branching and polymerization. Fructans occur in plants as carbohydrate reserves. As a natural product the fructans have an unpredictable length.

The fructans inulin and sinistrin are used in particular as markers in kidney function tests. Inulin and sinistrin are composed of 10 to 40 fructose units with a corresponding molecular weight of 1600 to 6500 Da. After intravenous injection, inulin and sinistrin are neither changed nor stored in the organism, but they are filtered out by the kidney glomeruli and are not reabsorbed again in the tubuli. The filtration of the fructans may vary according to their size.

In order to assess kidney function, it is usual to determine the time variation of the concentration of the marker in the blood after intravenous injection of said marker. To do so, blood samples have to be drawn. The concentration marker in the blood may, for example, be determined by enzymatic methods, as described in Kuehnle et al., Nephron, 62, 104-107 (1992). This method is time consuming, very cumbersome and of limited use.

A simpler alternative, based on fluorescein isothiocyanate labelled inulin (FITC-inulin) was described (M. Sohtell et al., Acta Physiol. Scand 119, 313-316 (1983); J. N. Lorenz and E. Gruenstein, Am. J. Physiol. (Renal Physiol. 45) 276, F172-F177 (1999). With this approach, also, blood is sampled and the fluorescein label of the FITC-Inulin is determined in the plasma. A very serious problem with this approach is that hemolysis, occurring during blood sampling, affects the determination of the concentration. Moreover, hemoglobin absorbs the excitation light at 480 nm very well, so less light is emitted and the apparent concentration is lower than in reality.

A disadvantage of inulin and FITC-inulin for the clinical routine analyses is their very low solubility in water. Hence the preparations containing insulin and FITC-insulin have to be heated to 90° C. until complete dissolution (Rieg, T. A High-throughput Method for Measurement of Glomerular Filtration Rate in Conscious Mice. J. Vis. Exp. (75), e50330, doi:10.3791/50330 (2013)), as their aqueous solutions tend to crystallize during storage. Unfortunately, this causes a partial degradation of inulin to fructose. Furthermore, the solution has to be then dialysed for 24 hr at room temperature. This step is especially important to FITC-inulin in order to remove unconjugated FITC, but also the byproducts generated by the heating procedure. Dialysis substantially decreases the concentration of FITC-inulin. In addition, the low solubility of inulin and FITC-inulin makes it difficult to achieve a well defined concentration and to handle the marker during the injection.

Recently, a Cy5.5-inulin conjugate has been introduced by Perkin-Elmer (GFR-Vivo; application note by Peterson, J. D, Perkin-Elmer Corporation). An advantage of Cy5.5-inulin conjugate over FITC-inulin is related to the excitation/emission wavelengths of Cy5.5 (675/705 nm). The longer wavelength of Cy5.5 allows a deeper tissue penetration, but its use with a small animal imager requires the animals being anesthetized. Anesthesia, however, has an unpredictable impact on blood pressure (initial rise, decrease during the major phase of anesthesia, followed by a rise at the ending phase). Kidney perfusion and thus GFR are highly sensitive to blood pressure, with low blood pressure values resulting in low GFR values. Thus, a meaningful/reproducible GFR measurement is not possible under anesthesia.

A substantial improvement over the previous art was the introduction of a FITC-sinistrin conjugate as described in U.S. Pat. No. 6,995,019. This marker is much more water soluble than FITC-inulin and, in addition, no undesired circulatory reactions have been observed when using FITC-sinistrin. Furthermore its concentration change over time can be measured transcutaneously. There is, however, still the problem of the penetration depth into the skin at a given wave length (480 nm allow a depth of only a few mm) and thus the dosage of the marker has to be fairly high to obtain a clear (measurement) signal. Another problem of the transcutaneous measurement is skin pigmentation, as melanin in the skin absorbs light quite efficiently at 480 nm.

A major disadvantage of inulin and also sinistrin is that they are natural products; their composition is quite variable even within the same batch, and even more in different batches. For Regulatory Affairs this is not acceptable.

OBJECT AND SUMMARY OF THE INVENTION

The object of the present invention is to provide a novel substance which can be used as marker in a kidney function test which overcome the disadvantages of the markers known in the prior art.

According to the invention, the above object is achieved thanks to the matter specified in the ensuing claims, which are understood as forming an integral part of the present invention.

The invention relates to fluorescent tricarbocyanine-cyclodextrin(s) conjugates as markers for kidney function tests in mammals.

An embodiment of the present invention relates to a fluorescent compound of formula (I)

$$F\text{-}L_n\text{-}CD_n \quad (I)$$

wherein

F is a tricarbocyanine residue of formula (II)

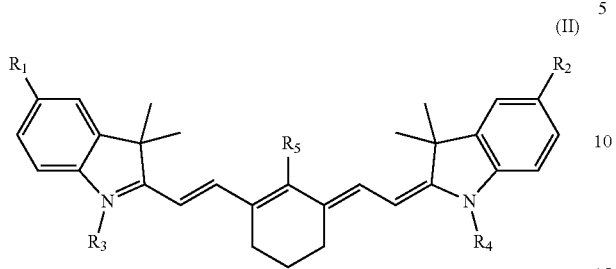

wherein $R_1$ and $R_2$ are independently selected from H, $SO_3H$, $CO_2H$, $SO_2NH_2$, $CH_2COOH$, $NH_2NHCOCH_2I$, $NO_2$, BR, CL, $CH_3$;

$R_3$ and $R_4$ are independently selected from $C_{1-4}$ alkyl, $(CH_2)_3C\equiv CH$, $(CH_2)_4C\equiv CH$ $(CH_2)_5COOH$, $(CH_2)_3SO_3H$, $(CH_2)_4SO_3H$, $(CH_2)_3NH_2$, $(CH_2)_4NH_2$, $(CH_2)_3N^+(CH_3)_3$, $(CH_2)_5N^+(CH_3)_3$, $(CH_2)_3N_3$, $(CH_2)_4N_3$, $(CH_2)_3NHCOCH_2I$, $(CH_2)_4NHCOCH_2I$; $(CH_2CH_2O)_2CH_3$, $(CH_2CH_2O)_3CH_3$ $(CH_2CH_2O)_4CH_3$;

$R_5$, is H, Cl, or

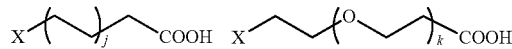

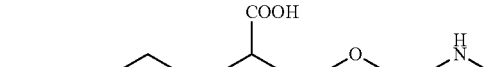

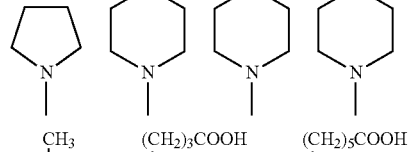

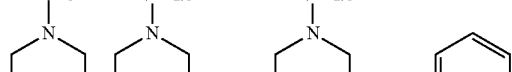

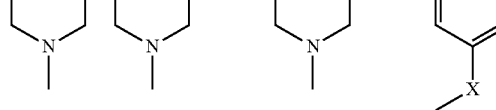

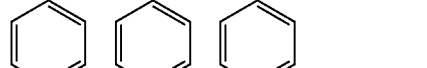

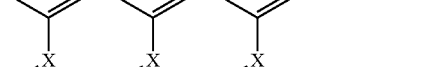

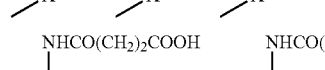

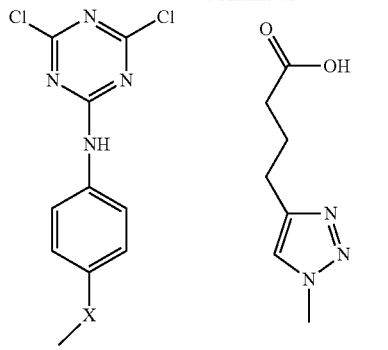

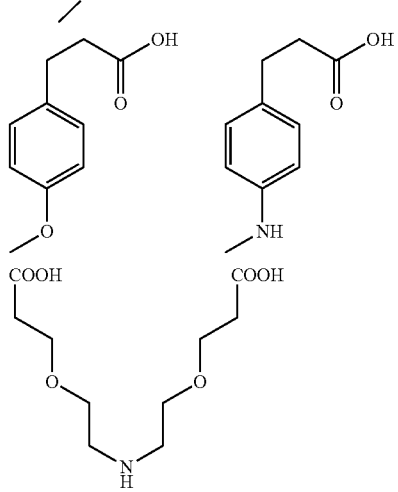

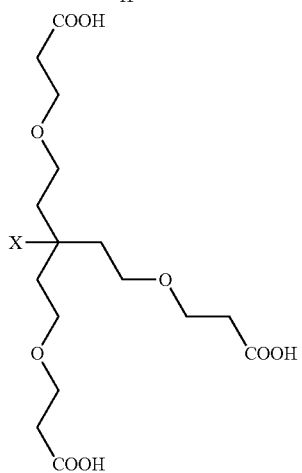

wherein

X is selected from NH, O, S;

j is an integer from 1 to 4;

k is an integer from 1 to 4;

CD is a cyclodextrin residue of formula (III)

wherein m is and integer equal to 6, 7 or 8,

R', R", R'" are independently selected from OH, $OCH_3$, $OCH_2CH_3$, $OCH_2CHOHCH_3$, $OCHOHCH_3$, $OCH_2COOH$, $O(CH_2)_4SO_3H$, $N_3$, $NH_2$, $NHCOCH_3$, $OCH_2C\equiv CH$, SH;

L is a linker group resulting from the coupling of the tricarbocyanine of formula (II) to the cyclodextrin(s) of formula (III) according to the following Table 1:

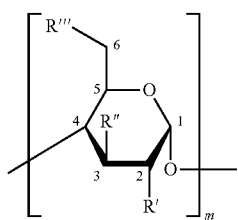

(III)

| Functional group of the tricarbocyanine (F) in any of the groups $R_3$, $R_4$ or $R_5$ | Functional group of the cyclodextrin (CD) in any of the groups R', R" or R''' | Linker group (L) |
|---|---|---|
| COOH | OH | —C(O)O— |
| COOH | $NH_2$ | —C(O)NH— |
| NCS | OH | —NC(S)O— |
| NCS | $NH_2$ | —NC(S)NH— |
| $NH_2$ | COOH | —NHC(O)— |
| $NHCOCH_2I$ | SH | $NHC(O)CH_2S$— |
| C≡CH | $N_3$ | ![triazole] |
| $N_3$ | C≡CH | ![triazole] |
| dichlorotriazine | OH | ![structure] |
| dichlorotriazine | OH, OH | ![structure] |
| dichlorotriazine | OH, $NH_2$ | ![structure] | n is an integer from 1 to 4,
and salts thereof.

A further embodiment of the present invention relates to a diagnostic formulation comprising at least one fluorescent compound of formula (I) for use in diagnostic tests for determining the kidney function parameters, preferably the glomerular filtration rate (GFR), of a mammal.

A still further embodiment of the present invention relates to a diagnostic method for determining whether a mammal suffers from chronic kidney diseases, wherein the method comprises i) administering at least one fluorescent compound of formula (I) or a diagnostic formulation comprising at least one compound of formula (I) to the mammal, and ii) detecting and measuring the fluorescence emitted by the fluorescent compound, wherein the measured fluorescence directly correlates (i.e. correlates in a proportional way) with the kidney function, particularly the glomerular filtration rate (GFR), of the mammal.

A further embodiment of the present invention relates to a method for screening pharmaceutical compounds suitable for treatment of chronic kidney diseases, wherein the method comprises:

i) administering to an animal model of chronic kidney disease a pharmaceutical compound and at least one fluorescent compound of formula (I), wherein the fluorescent compound is administered subsequently to the pharmaceutical compound;

ii) measuring the glomerular filtration rate by detecting and measuring the fluorescence emission of the at least one fluorescent compound of formula (I), wherein the detection and the measurement of the fluorescence comprises the detection and the measurement of the fluorescent emission emerging from the skin of the animal model in response to excitation with a red light or near infrared light source; and iii) selecting the pharmaceutical compound that increases glomerular filtration rate (GFR).

BRIEF DESCRIPTION OF THE DRAWINGS

The invention will now be described, by way of example only, with reference to the enclosed figures of drawing, wherein.

DETAILED DESCRIPTION OF THE INVENTION

Figure 1:
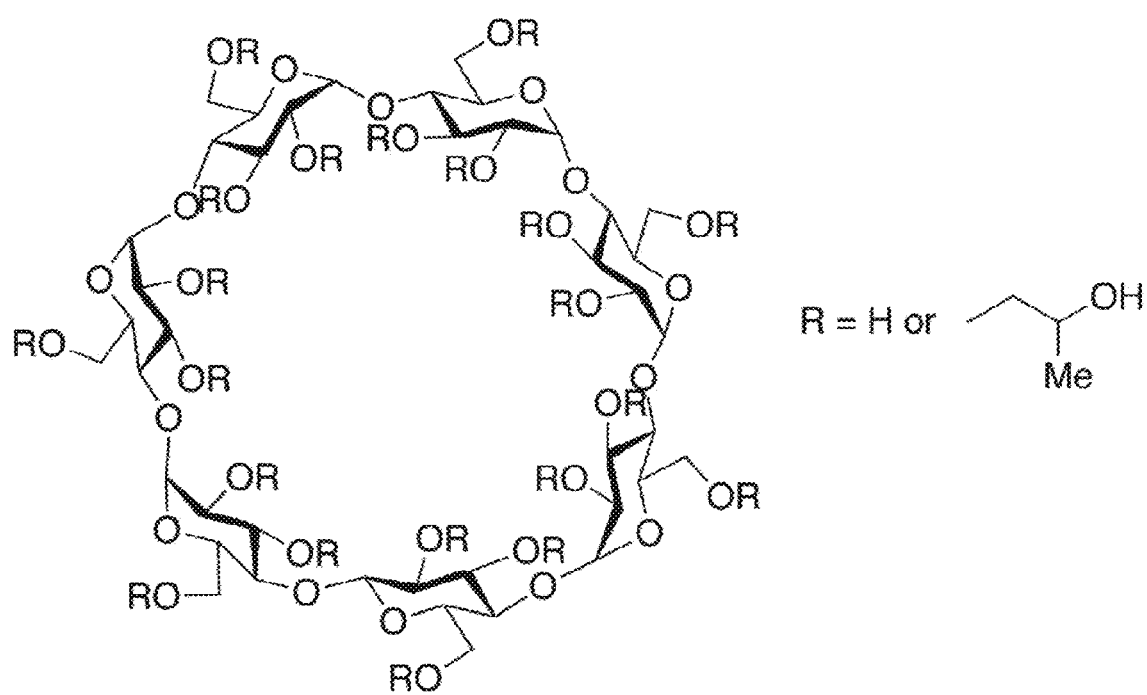
FIG. 1: Structural formula of 2-hydroxypropyl-β-cyclo-dextrin (HβCD).

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The invention relates to fluorescent tricarbocyanine-cyclodextrin(s) conjugates as markers for kidney function tests.

These fluorescent conjugates, that are the object of the present invention, are represented by the general formula (I)

$$F-L_n-CD_n \quad (I)$$

wherein
F is a tricarbocyanine residue of formula (II)

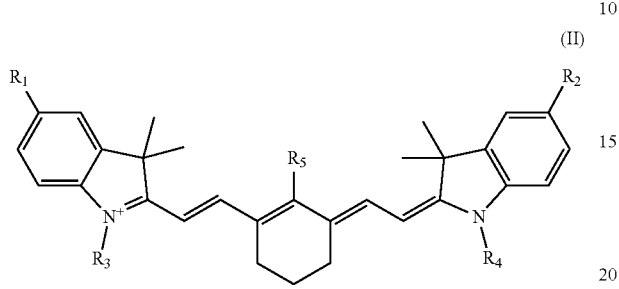

(II)

wherein
$R_1$ and $R_2$ are independently selected from H, $SO_3H$, $CO_2H$, $SO_2NH_2$, $CH_2COOH$, $NH_2$, $NHCOCH_2I$, $NO_2$, Br, Cl, $CH_3$;

$R_3$ and $R_4$ are independently selected from $C_{1-4}$ alkyl, $(CH_2)_3C\equiv CH$, $(CH_2)_4C\equiv CH(CH_2)_5COOH$, $(CH_2)_3SO_3H$, $(CH_2)_4SO_3H$, $(CH_2)_3NH_2$, $(CH_2)_4NH_2$, $(CH_2)_3N^+(CH_3)_3$, $(CH_2)_5N^+(CH_3)_3$, $(CH_2)_3N_3$, $(CH_2)_4N_3$, $(CH_2)_3NHCOCH_2I$, $(CH_2)_4NHCOCH_2I$; $(CH_2CH_2O)_2CH_3$, $(CH_2CH_2O)_3CH_3(CH_2CH_2O)_4CH_3$;

$R_5$, is H, Cl, or

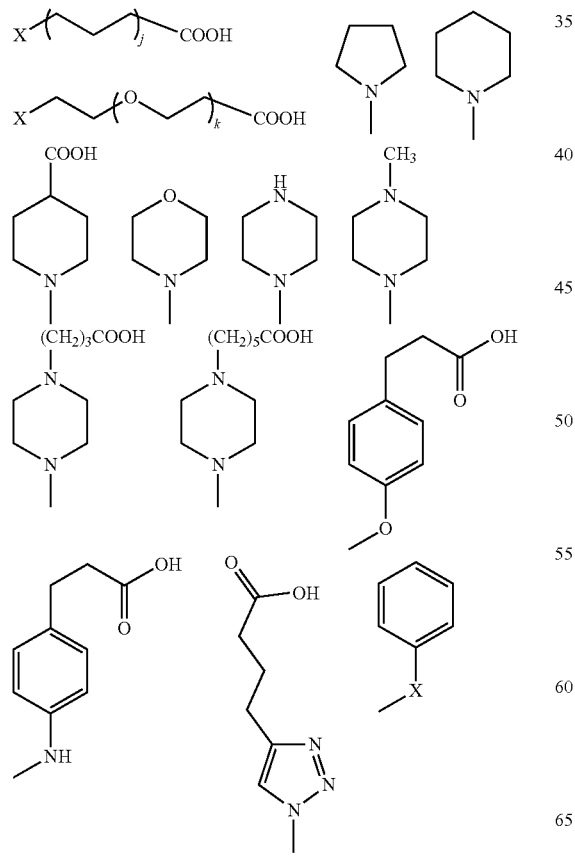

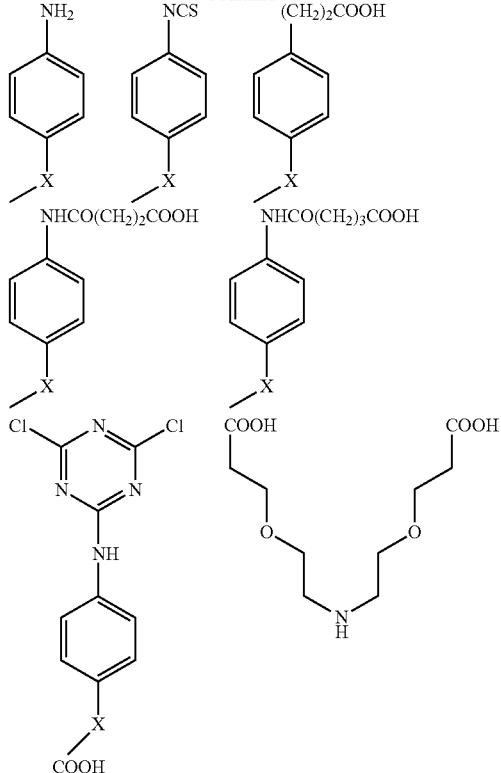

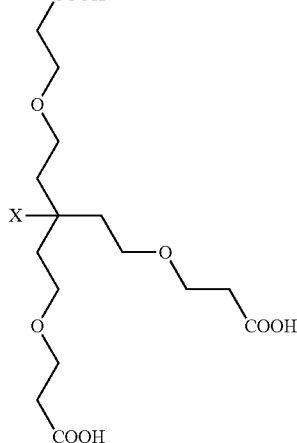

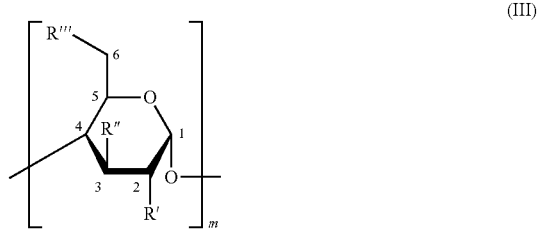

wherein
X is selected from NH, O, S;
j is an integer from 1 to 4;
k is an integer from 1 to 4;
CD is a cyclodextrin residue of formula (III)

(III)

wherein m is and integer equal to 6, 7 or 8,

R', R", R'" are independently selected from OH, $OCH_3$, $OCH_2CH_3$, $OCH_2CHOHCH_3$, $OCHOHCH_3$, $OCH_2COOH$, $O(CH_2)_4SO_3H$, $N_3$, $NH_2$, $NHCOCH_3$, $OCH_2C \equiv CH$, SH;

L is a linker group resulting from the coupling of the tricarbocyanine of formula (II) to the cyclodextrin(s) of formula (III) according to the following Table 1:

| Functional group of the tricarbocyanine (F) in any of the groups $R_3$, $R_4$ or $R_5$ | Functional group of the cyclodextrin (CD) in any of the groups R', R" or R'" | Linker group (L) |
|---|---|---|
| COOH | OH | —C(O)O— |
| COOH | $NH_2$ | —C(O)NH— |
| NCS | OH | —NC(S)O— |
| NCS | $NH_2$ | —NC(S)NH— |
| $NH_2$ | COOH | —NHC(O)— |
| $NHCOCH_2I$ | SH | $NHC(O)CH_2S$— |
| $C \equiv CH$ | $N_3$ | [triazole structure] |
| $N_3$ | $C \equiv CH$ | [triazole structure] |
| dichlorotriazine | OH | [triazine structure] |
| dichlorotriazine | OH, OH | [triazine structure] |
| dichlorotriazine | OH, $NH_2$ | [triazine structure] | n is an integer from 1 to 4, and salts thereof.

Dyes belonging to the class of cyanines have already found some use in clinical diagnostics; in particular, Indocyanine Green has been used for kidney function test and fluorescence angiography for more than 30 years.

Tricarbocyanine dyes absorb and emit light in the near-infrared region (NIR) (650-900 nm). Tricarbocyanine dyes are especially suitable for in vivo imaging, diagnostics and even therapeutics, since biological tissues are relatively poor absorbers in the near-infrared spectral region, and infrared light can penetrate deeply in such tissues; in addition, these dyes do not give origin (or at very low amount) to autofluorescence in the near-infrared spectral region.

Cyclodextrins (CD) are cyclic oligosaccharides produced by the enzymatic degradation of starch. Depending on reaction conditions, three main CDs can be obtained α, β and γ; they consist of 6, 7 or 8 glucopyranose units. They are shaped as a truncated cone, with hydroxyl groups on each side. Their cavity is constituted by the glucosidal moieties. These three dimensional structures result in a high external hydrophilicity and internal hydrophobicity.

In one embodiment, CDs are selected from β- and γ-cyclodextrins, that is, CD in which m parameter of formula (III) has a value about of 7 (β-cyclodextrin) or 8 (γ-cyclodextrin), respectively.

While the water solubility of natural CDs is limited, chemical substitution at the 2-, 3- and 6-hydroxyl sites (i.e., when R', R" and R'" are OH) greatly increases solubility. Most of cyclodextrins modified in this way, are able to achieve a 50% (w/v) concentration in water.

In one embodiment, at least one of the groups R', R", R'"0 of formula (III) is selected from $OCH_3$, $OCH_2CH_3$, $OCH_2CHOHCH_3$, provided that at least one group R', R", R'" is OH.

In a preferred embodiment, R' and R" are OH, R'" is selected from $OCH_3$, $OCH_2CH_3$, $OCH_2CHOHCH_3$, preferably is $OCH_2CHOHCH_3$, in which the substitution degree of R'" is between 0.5 and 1.5 per unit of formula (III).

It is known to the skilled technician that the substitution of the groups R', R", R'" of a cyclodextrin molecule, for example with groups $OCH_3$, $OCH_2CH_3$, $OCH_2CHOHCH_3$, is partial, i.e. it that takes place only in some of the m structures of formula (III) constituting the cyclodextrin with a substitution degree between 0.5 and 1.5 substituents per unit of formula (III); in other words, some groups R', R", R'" in some of the m structures of formula (III) are not replaced, or are OH groups, and are the ones predominantly, though not exclusively, involved in the conjugation with tricarbocyanine molecules of formula (II).

Figure 2:
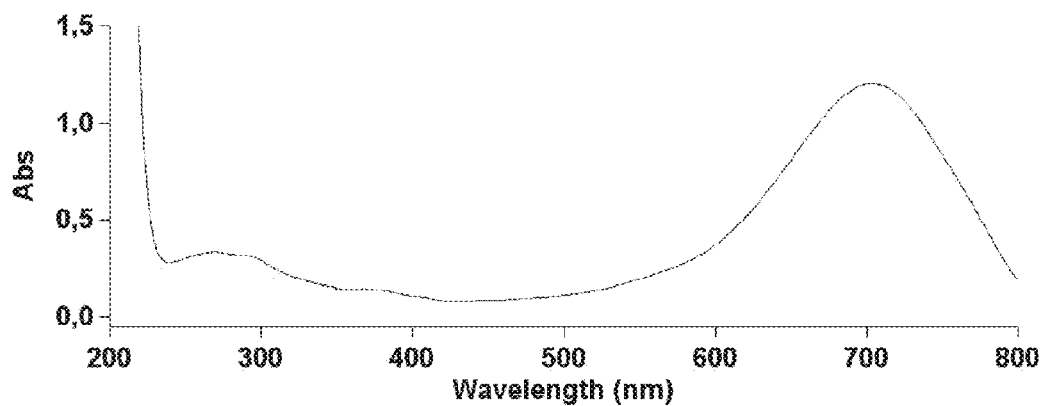
FIG. 2: Absorption spectrum of ABZWCY-HβCD in methanol.

In a further preferred embodiment, cyclodextrins of formula (III) are selected from 2-hydroxypropyl cyclodextrins (HCD), and in particular 2-hydroxypropyl-β-cyclodextrin (HβCD, whose chemical structure is shown in FIG. 2, and 2-hydroxypropyl-γ-cyclodextrin (HγCD).

HβCD and HγCD have been found to be non-toxic in mice and rabbits [Pitha, J. "Amorphous water soluble derivatives of cyclodextrins: non toxic dissolution enhancing excipients." *J. Pharm. Sci.* 1985, 74, 987]. HβCD and HγCD are widely used to improve the water solubility of drugs.

HβCD and HγCD represent advantageous substitutes of fructans, such as inulin and sinistrin, as components of fluorescent markers for the determination of GFR, as they are relatively inexpensive, non-toxic, structurally well-defined, synthetic products, with a strong solubilizing power.

In an embodiment, the conjugate of formula (I) presents from 1 to 4 linker groups L to allow conjugation of 1 to 4 cyclodextrin molecules to one tricarbocyanine molecule.

In a preferred embodiment, $R_1$ and $R_2$ groups are independently selected from H, $SO_3H$, $CO_2H$.

In a preferred embodiment, $R_3$ and $R_4$ groups are independently selected from methyl, ethyl, $(CH_2)_5COOH$, $(CH_2)_4SO_3H$, $(CH_2)_3N^+(CH_3)_3$.

In a preferred embodiment, R₅ group is selected from H, Cl, or

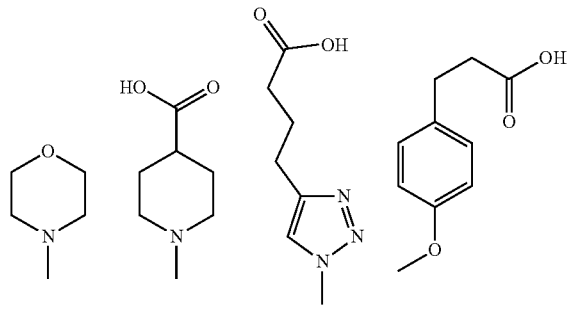

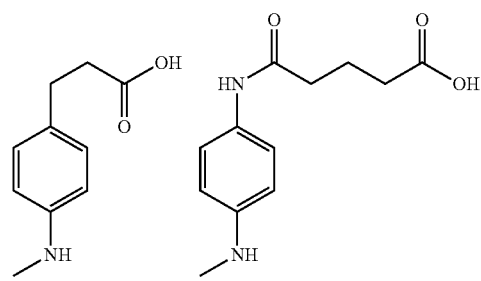

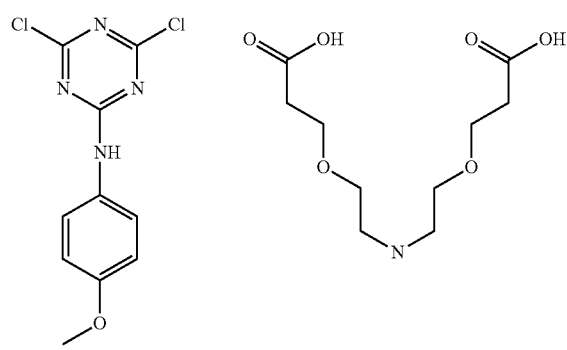

In a preferred embodiment, the linker group L is selected from an ester, an ether, an amide, a thiocarbamate, a thiourea, a thioether, a 1,2,3-triazole, or

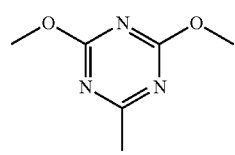

In a preferred embodiment, the fluorescent tricarbocyanine-cyclodextrin conjugate is a compound of formula (IV):

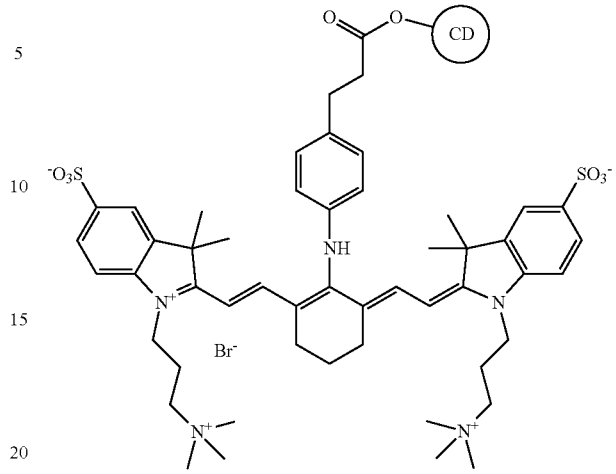

wherein CD is 2-hydroxypropyl-β-cyclodextrin (HβCD) or 2-hydroxypropyl-γ-cyclodextrin (HγCD) and the linker L of Formula (I) (corresponding to the value of the n parameter of formula (I) equal to 1) is an ester bond formed in the coupling reaction of the carboxyl group of the tricarbocyanine

(corresponding to carboxyl group of R₅ group = )

with a residue group R'''=OH of CD.

In a preferred embodiment, the fluorescent tricarbocyanine-cyclodextrin conjugate is a compound of formula (V):

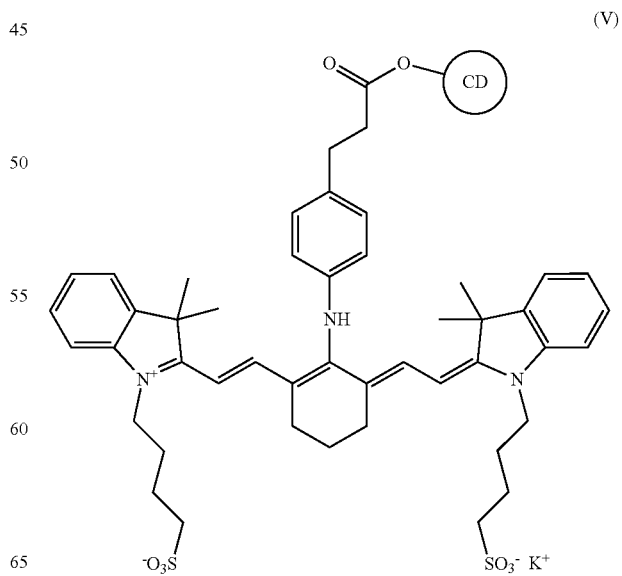

wherein CD is 2-hydroxypropyl-β-cyclodextrin (HβCD) or 2-hydroxypropyl-γ-cyclodextrin (HγCD) and the linker L of Formula (I) (corresponding to the value of the n parameter of formula (I) equal to 1) is an ester bond formed in the coupling reaction of the carboxyl group of the tricarbocyanine (corresponding to carboxyl group of $R_5$ group = 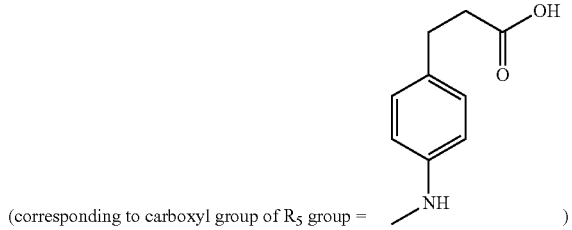 )

with a residue group R'''=OH of CD.

In a preferred embodiment, the fluorescent tricarbocyanine-cyclodextrin conjugate is a compound of formula (VI):

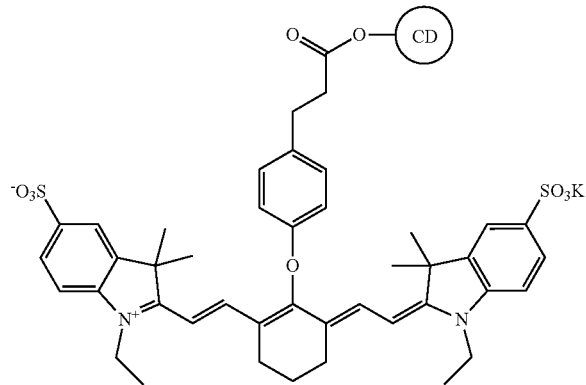

(VI)

wherein CD is 2-hydroxypropyl-β-cyclodextrin (HβCD) or 2-hydroxypropyl-γ-cyclodextrin (HγCD) and the linker L of Formula (I) (corresponding to the value of the n parameter of formula (I) equal to 1) is an ester bond formed in the coupling reaction of the carboxyl group of the tricarbocyanine (corresponding to carboxyl group of $R_5$ group = 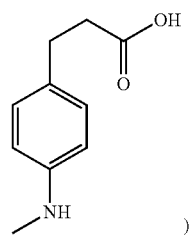 )

with a residue group R'''=OH of CD.

In a preferred embodiment, the fluorescent tricarbocyanine-cyclodextrin conjugate is a compound of formula (VII):

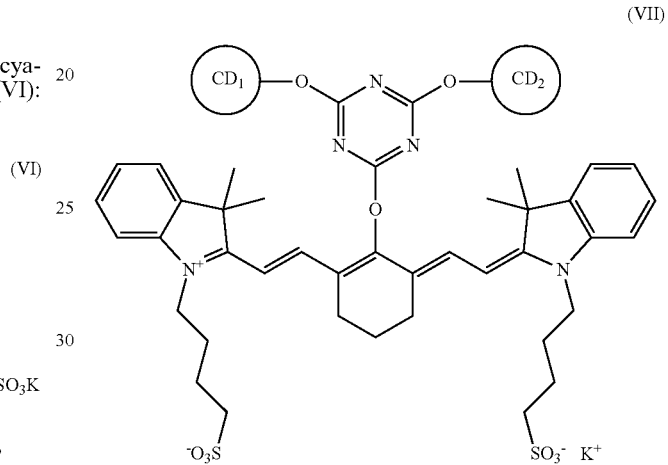

(VII)

wherein $CD_1$ and $CD_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ether bonds formed in the coupling reaction of the $R_5$ group=dichlorotriazine of the tricarbocyanine with a residue group R'''=OH of $CD_1$ and $CD_2$, respectively.

In a preferred embodiment, the fluorescent tricarbocyanine-cyclodextrin conjugate is a compound of formula (VIII):

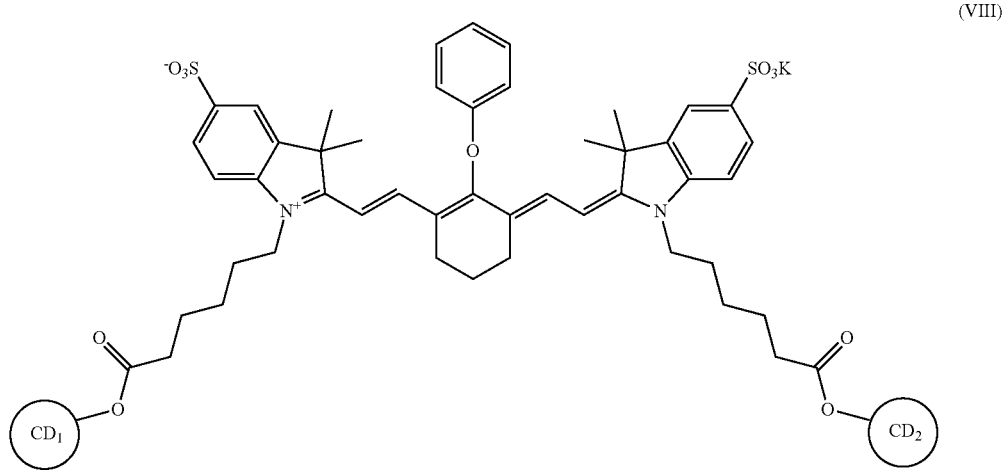

(VIII)

wherein $CD_1$ and $CD_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine (corresponding to the carboxyl group of the $R_3$ and $R_4$ groups=$(CH_2)_5COOH$) with a residue group $R'''$=OH of $CD_1$ and $CD_2$, respectively.

In a preferred embodiment, the fluorescent tricarbocyanine-cyclodextrin conjugate is a compound of formula (IX):

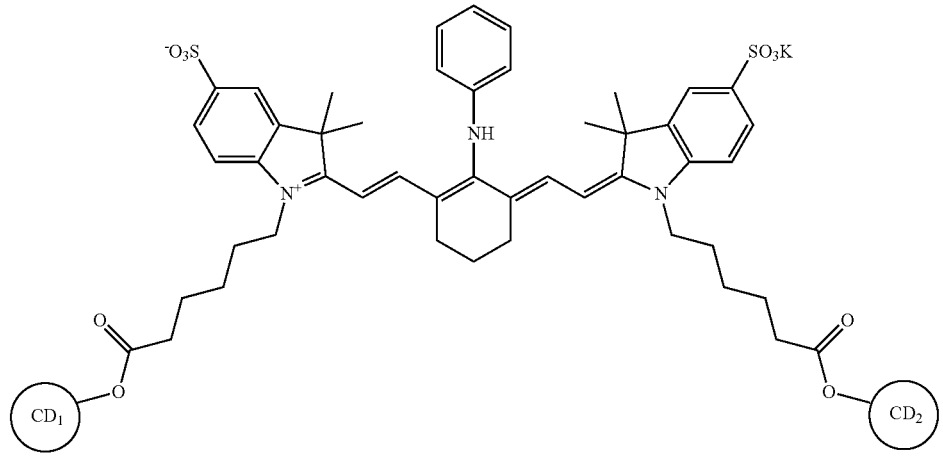

(IX)

wherein $CD_1$ and $CD_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine (corresponding to the carboxyl group of the $R_3$ and $R_4$ groups=$(CH_2)_5COOH$), with a residue group $R'''$=CH of $CD_1$ and $CD_2$, respectively.

In a preferred embodiment, the fluorescent tricarbocyanine-cyclodextrin conjugate is a compound of formula (X):

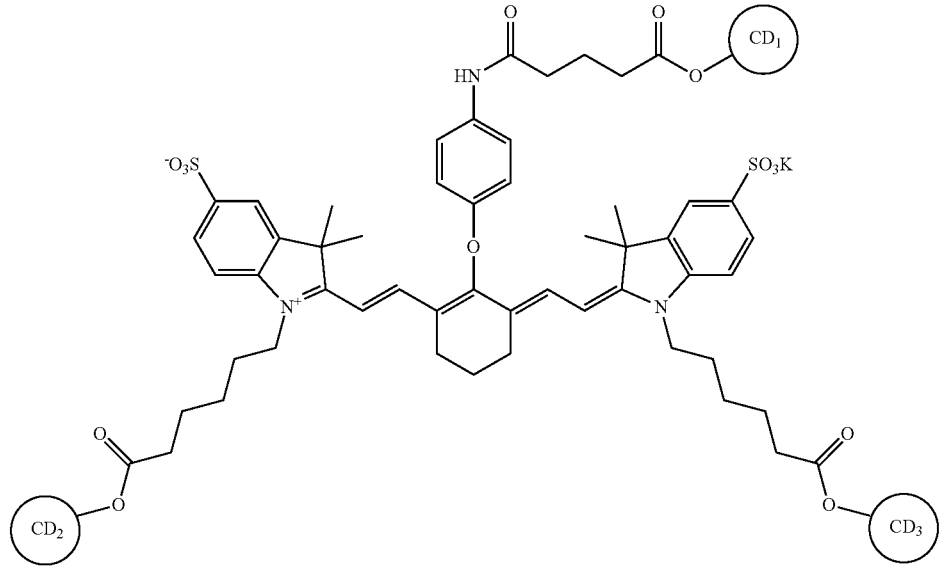

(X)

wherein $CD_1$, $CD_2$ and $CD_3$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 3) are ester bonds formed in the respective coupling reaction of a carboxyl group of the tricarbocyanine

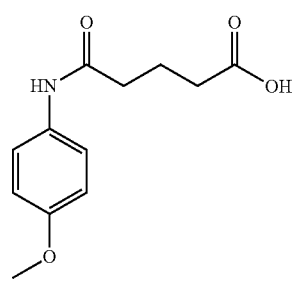

(corresponding to carboxyl group of $R_3$ and $R_4$ groups = $(CH_2)_5COOH$ and the carboxyl group of the $R_5$ group = )

with a residue group $R'''$=OH of $CD_1$, $CD_2$, and $CD_3$, respectively.

In a preferred embodiment, the fluorescent tricarbocyanine-cyclodextrin conjugate is a compound of formula (XI):

wherein $CD_1$, $CD_2$ and $CD_3$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 3) are ester bonds formed in the respective coupling reaction of a carboxyl group of the tricarbocyanine

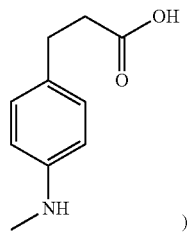

(corresponding to carboxyl group of $R_3$ and $R_4$ groups = $(CH_2)_5COOH$ and the carboxyl group of the $R_5$ group = )

with a residue group $R'''$=OH of $CD_1$ $CD_2$ and $CD_3$, respectively.

In a preferred embodiment, the fluorescent tricarbocyanine-cyclodextrin conjugate is a compound of formula (XII):

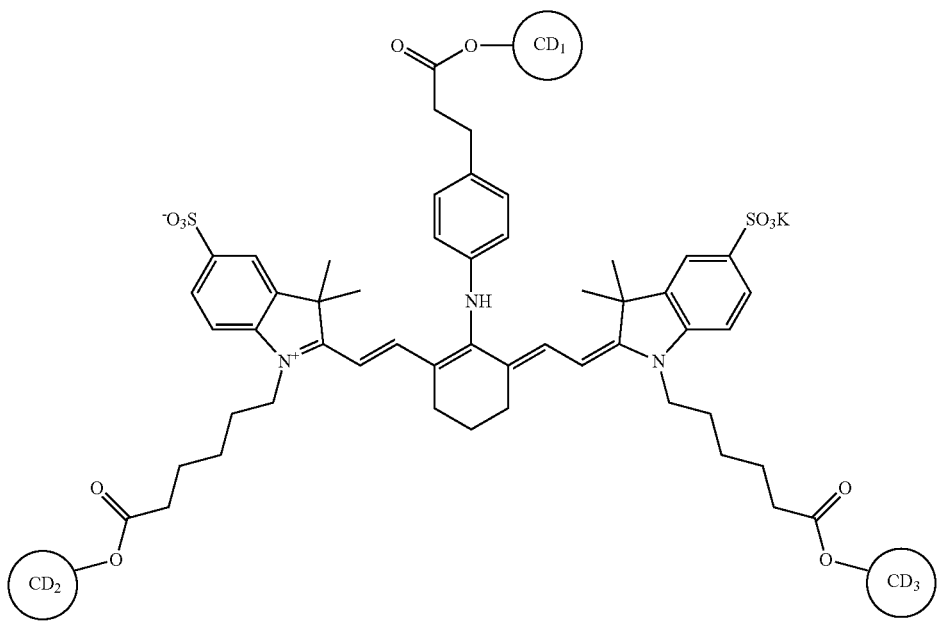

(XI)

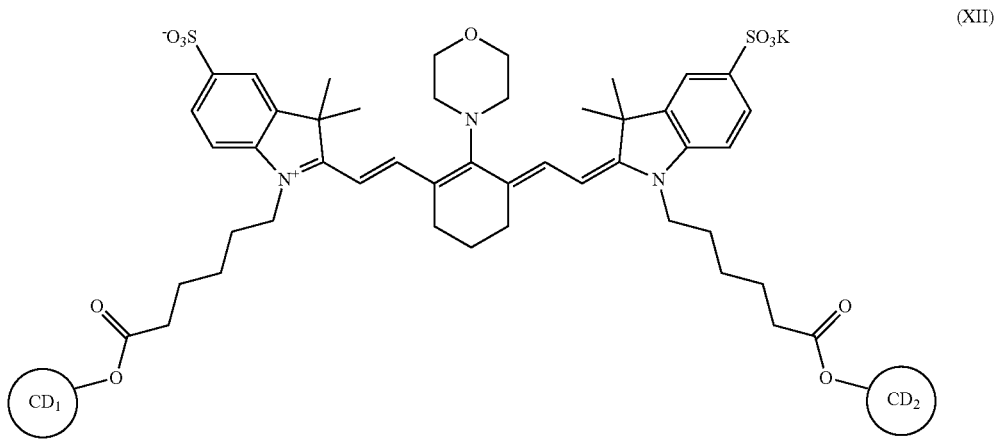
(XII)

wherein $CD_1$ and $CD_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine (corresponding to the carboxyl group of the $R_3$ and $R_4$ groups $(CH_2)_5COOH$) with a residue group $R'''$=OH of $CD_1$ and $CD_2$, respectively In a preferred embodiment, the fluorescent tricarbocyanine-cyclodextrin conjugate is a compound of formula (XIII):

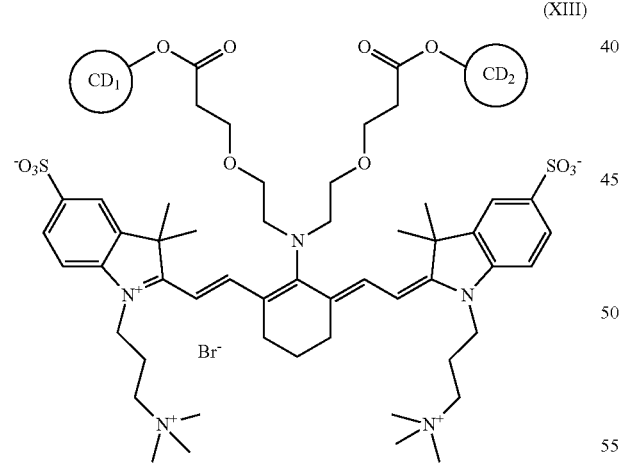
(XIII)

wherein $CD_1$ and $CD_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine (corresponding to the carboxyl group of the $R_5$ group = 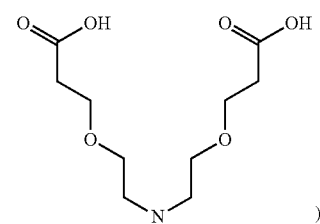 )

with a residue group $R'''$=OH of $CD_1$ and $CD_2$, respectively.

In a preferred embodiment, the fluorescent tricarbocyanine-cyclodextrin conjugate is a compound of formula (XIV):

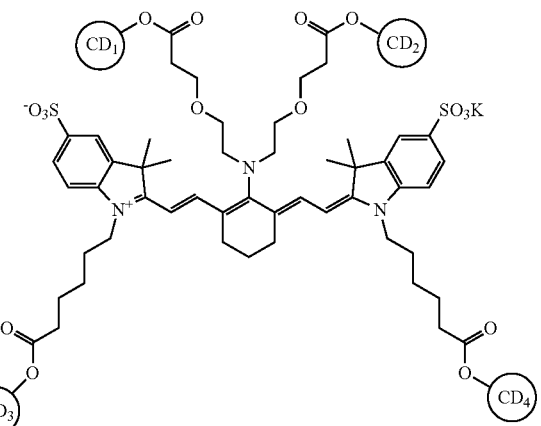
(XIV)

wherein $CD_1$, $CD_2$, $CD_3$ and $CD_4$ are, independently, 2-hydroxypropyl-β-cyclodextrin (HβCD) or 2hydroxypropyl-γ-cyclodextrin (HγCD) and the linkers L of Formula (I) (corresponding to the value of the n parameter of formula (I) equal to 4) are ester bonds formed in the respective coupling reaction of a carboxyl group of the tricarbocyanine

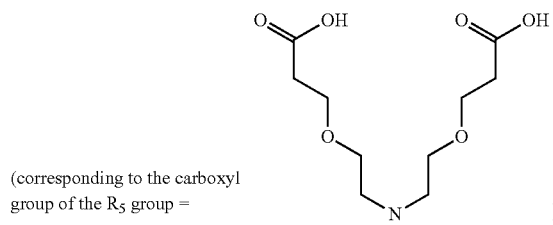

(corresponding to the carboxyl group of the R$_5$ group = )

with a residue group R'''=OH of CD$_1$ and CD$_2$, CD$_3$ and CD$_4$, respectively.

In a preferred embodiment, the fluorescent tricarbocyanine-cyclodextrin conjugate is a compound of formula (XV):

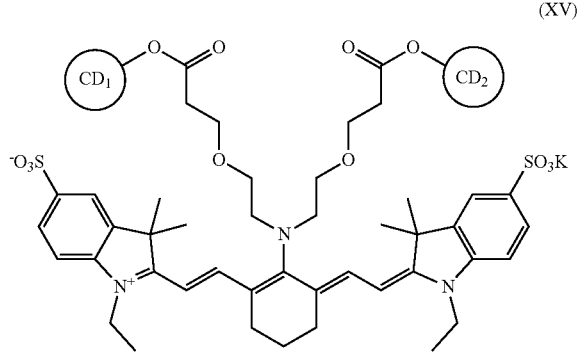

(XV)

wherein CD$_1$ and CD$_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine

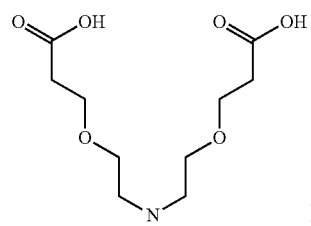

(corresponding to the carboxyl group of the R$_5$ group = )

with a residue group R'''=OH of CD$_1$ and CD$_2$, respectively

In a preferred embodiment, the fluorescent tricarbocyanine-cyclodextrin conjugate is a compound of formula (XVI):

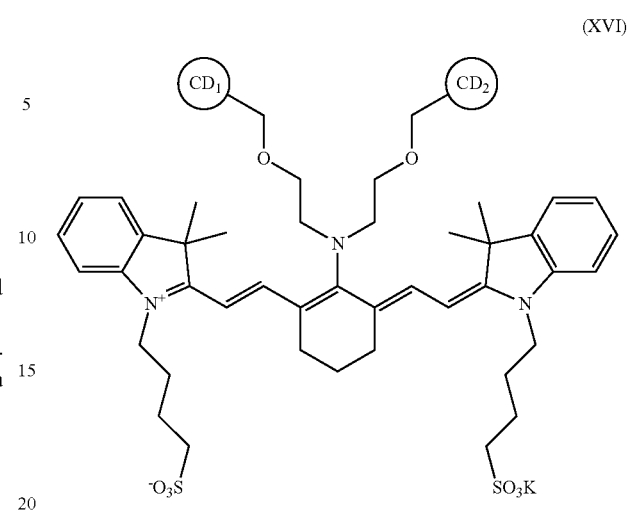

(XVI)

wherein CD$_1$ and CD$_2$ are, independently, 2-hydroxypropyl-β-cyclodextrin (HβCD) or 2-hydroxypropyl-γ-cyclodextrin (HγCD) and the linkers L of Formula (I) (corresponding to the value of the n parameter of formula (I) equal to 2) are ester bonds formed in the respective coupling reaction of a carboxyl group of the tricarbocyanine

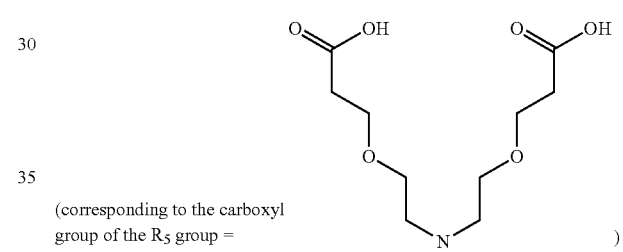

(corresponding to the carboxyl group of the R$_5$ group = )

with a residue group R'''=OH of, CD$_1$ and CD$_2$, respectively.

In a preferred embodiment, the fluorescent tricarbocyanine-cyclodextrin conjugate is a compound of formula (XVII):

(XVI)

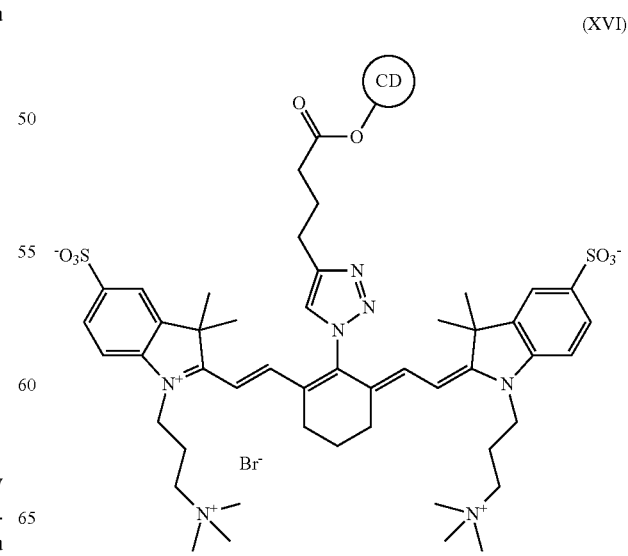

wherein CD is a 2-hydroxypropyl-β-cyclodextrin (HβCD) or 2-hydroxypropyl-γ-cyclodextrin (HγCD) and the linker L of Formula (I) (corresponding to the value of the n parameter of formula (I) equal to 1) is an ester bond formed in the respective coupling reaction of a carboxyl group of the tricarbocyanine

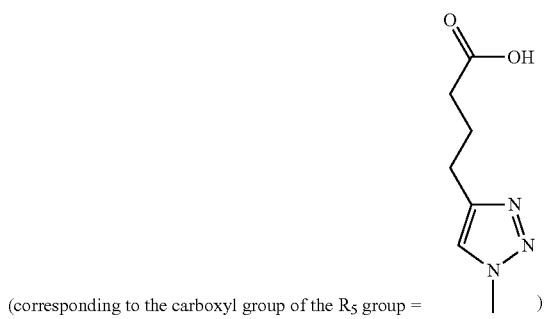

(corresponding to the carboxyl group of the $R_5$ group =          )

with a residue group R'''=OH of CD.

In a further embodiment, the present invention relates to the use of at least one fluorescent compound of formula (I) or a diagnostic formulation comprising at least one fluorescent compound of formula (I) in kidney diagnostics, preferably in measuring the glomerular filtration rate (GFR), in a mammal In an embodiment, the mammal is a mouse, a rat, a guinea pig, a cat, a dog, a sheep, a goat, a pig, a cow, a horse, a primate.

In a still further embodiment, the present disclosure relates to a method of diagnosing the glomerular filtration rate of a mammal, preferably the glomerular filtration rate (GFR), wherein at least one compound of formula (I) or a diagnostic formulation comprising at last a compound of formula (I) is administered to a mammal and the fluorescent signal emitted from the dye of compound of formula (I) is detected and measured.

Preferably, the at least one compound of formula (I) or the diagnostic formulation comprising at least one compound of formula (I) is administered to the mammal via a parenteral route.

The diagnostic method herein disclosed is non-invasive, because the detection and measurement of the fluorescence emitted from the at least one compound of formula (I) are realized by detecting and measuring the fluorescent emission emerging from the skin of the mammal in response to excitation with a red light or near infrared light source, preferably by means of a sensor device placed onto the mammal skin. The method is accomplished in a clinically relevant period of time. That is, that period of time is such to allow the absorption of the compound of formula (I) in the blood of the mammal and the following secretion by the kidney system.

In a further embodiment, a compound of formula (I) can be used for screening pharmaceutical compounds (test agents) suitable for treatment of chronic kidney diseases.

The screening method comprises:
i) administering to an animal model of chronic kidney diseases the test agent and at least one fluorescent compound of formula (I), wherein the fluorescent compound is administered subsequently to test agent;
ii) measuring the glomerular filtration rate by detecting and measuring the fluorescence emission of the at least one fluorescent compound, wherein the detection and the measurement of the fluorescence comprises the detection and the measurement of the fluorescent emission emerging from the skin of the animal model in response to excitation with a red light or near infrared light source;
iii) selecting the test agent that increases glomerular filtration rate.

Mammalian models of chronic kidney diseases in, for example, mice, rats, guinea pigs, cats, dogs, sheep, goats, pigs, cows, horses, and primates, may be created by causing an appropriate direct or indirect injury to the kidney tissue of the animal. Animal models of acute kidney failure may, for example, be created by inducing in the animal the conditions or diseases such as acute interstitial nephritis or acute tubular necrosis, for example by the controlled administration of nephrotoxic agents (e.g., antibiotics, aminoglycoside drugs, heavy metals).

Other mammalian models of chronic kidney disease are disclosed in Vukicevic, et al. (1987), *J. Bone Mineral Res.* 2:533; and EP-B-0 914 146; animal models have been described in detail in a handbook *Experimental and genetic rat models of chronic renal failure*, Gretz, N.; Strauch, M.; Karger (Basel and New York); 1993; pp 343; (ISBN 3805554990). Rat models of autosomal dominant polycystic kidney disease have been described in Gretz N, Kränzlin B, Pey R, Schieren G, Bach J, Obermöller N, Ceccherini I, Klöting I, Rohmeiss P, Bachmann S, Hafner M. *Nephrol Dial Transplant.* 1996; 11 Suppl 6:46-51. Review; murine models of polycystic kidney disease have been described in Schieren G, Pey R, Bach J, Hafner M, Gretz N. *Nephrol Dial Transplant.* 1996; 11 Suppl 6:38-45. Review.

The following examples are intended to illustrate particular aspects of the present invention and should not be construed as limiting the scope thereof as defined by the claims.

The following examples provide a detailed description of the synthesis of the tricarbocyanine named 2-((E)-2-((E)-2-((4-(2-carboxyethyl)phenyl)amino)-3-((E)-2-(3,3-dimethyl-5 -sulfonate-1-(3-trimethylammonium)propyl)indolin-2-ylidene)ethylidene)cyclohex-1-en-1-yl)vinyl)-3,3-dimethyl-1-(3-(trimethylammonium)propyl)-3H-indol-1-ium-5-sulfonate bromide (named ABZWCY), its conjugation to a cyclodextrin molecule and its use in a diagnostic method for determining GFR in a rat.

A fluorescent tricarbocyanine dye ABZWCY (4) was synthesized and linked to HβCD, according to Example 1 and Reaction Schemes 1-4.

The resulting ABZWCY-HβCD conjugate exhibited excellent water solubility with concentrations reaching more than 100 mg/mL. In addition it showed a low plasma protein binding (PPB), i.e. less than 10%, which is a lower value than $^{125}$I-iothalamate, one of the golden standard agent for the GFR measurement [Levey, A. S. et al. *J. Am. Soc. Nephrol.* 1993 4(5), 1159-1177].

The noninvasive real-time monitoring of plasma clearance resulted in a half-life of approximately 17±2 min. Moreover, the tricarbocyanine-cyclodextrin marker did not exhibit significant differences in plasma clearance half time in the absence and presence of a compound able to inhibit tubular secretion. This means that kidney tubular secretion is not a significant elimination pathway for these markers in a mammal. The present marker was exclusively cleared by the kidneys, with no appreciable nonspecific background signal in all the tissues and organs and only fluorescence signal remaining in the bladder 2 h post injection. In conclusion, such a fluorescent compound is highly suitable as exogenous fluorescent tracer for monitoring GFR.

EXAMPLE 1

Preparation of ABZWCY-HβCD a) Preparation of 2,3,3-Trimethyl-1-[3-(trimethylammonium)propyl]-3H-indolinium sulfonate bromide (1).

The reaction was carried out according to Scheme 1.

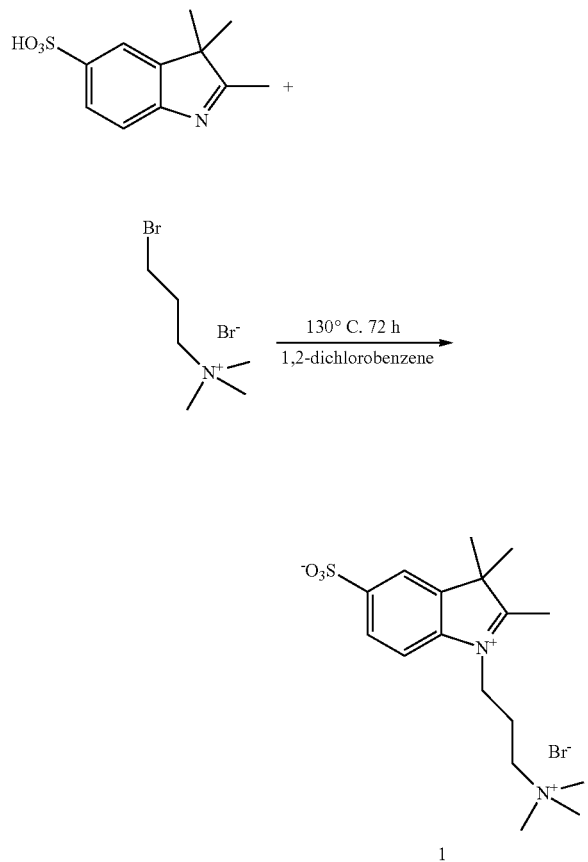

A mixture of 2,3,3-trimethyl-3H-indole-5-sulfonic acid (1.54 g, 6.5 mmol; (prepared according to Mujumdar et al., *Bioconjugate Chemistry* (1993), 4/2, 106) and (3-bromopropyl)trimethyl ammonium bromide (2.51 g, 9.5 mmol) in 1,2-dichlorobenzene (16 mL) was heated at 130° C. for 72 hours under argon flow. The reaction mixture was cooled to room temperature and the solvent was decanted. The crude product was washed with CH$_2$Cl$_2$, dissolved in acetone and reprecipitated into a large volume of ethyl acetate to afford a solid 1, which was used in the next step without further purification.

b) Preparation of 2-((E)-2-((E)-2-chloro-3-((E)-2-(3,3'-dimethyl-5-sulfonate-1-(3-(trimethylammonium)propyl)-indo-lin-2-ylidene)cyclohex-1-enyl)-3,3-dimethyl-1-(3-(trimethylammonium)-propyl)-3H-indolium-5-sulfonate bromide (3).

The reaction was carried out according to Scheme 2.

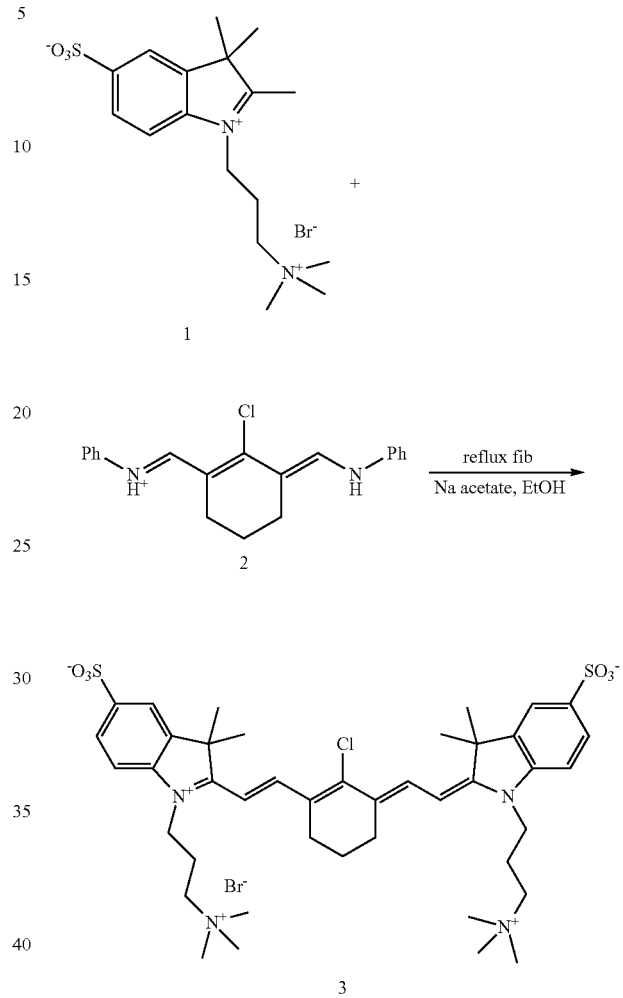

A mixture of bromide salt 1 (0.5 g, 1.48 mmol), Vilsmeier-Haack reagent 2 (0.265 g, 0.73 mmol; prepared according to Makin S. M.; Boiko, L. I.; Shavrigina, O. A. *Zh. Org. Khim.* 1977, 13, 1189) and anhydrous sodium acetate (0.246 g, 3 mmol) was refluxed in 10 ml of absolute ethanol for 6 h under argon flow. The reaction mixture was cooled to room temperature, and then concentrated under reduced pressure to yield a brown-green residue. The crude product was washed with dichloromethane and the residue was suspended in methanol/dichloromethane (1/4, 100 mL), filtered and dried in vacuo to yield a golden-green solid (3) 505 mg, yield=84.9%.

$^1$HNMR (400 MHz, DMSO-d$_6$) δ1.72 (s, 12H), 1.88 (m, 2H), 2.18 (m, 4H), 2.76 (m, 4H), 3.08 (s, 18H), 3.49 (m, 4H), 4.18 (m, 4H) m 6.36 (d), 7.45 (d) 7.85 (s, 2H), 8.31 (d, 2H). Absorption max (MeOH) 777 nm (methanol). Emission max (MeOH): 810 nm.

c) Preparation of 2-((E)-2-((E)-2-((4-(2-carboxyethyl)phenyl)amino)-3-((E)-2-(3,3-dimethyl-5-sulfonate-1-(3-trimethylammonium)propyl)indolin-2-ylidene)ethylidene)-cyclohex-1-en-1-yl)vinyl)-3,3-dimethyl-1-(3-(trimethylammonium)propyl)-3H-indol-1-ium-5-sulfonate bromide (ABZWCY, 4).

The reaction was carried out according to Scheme 3.

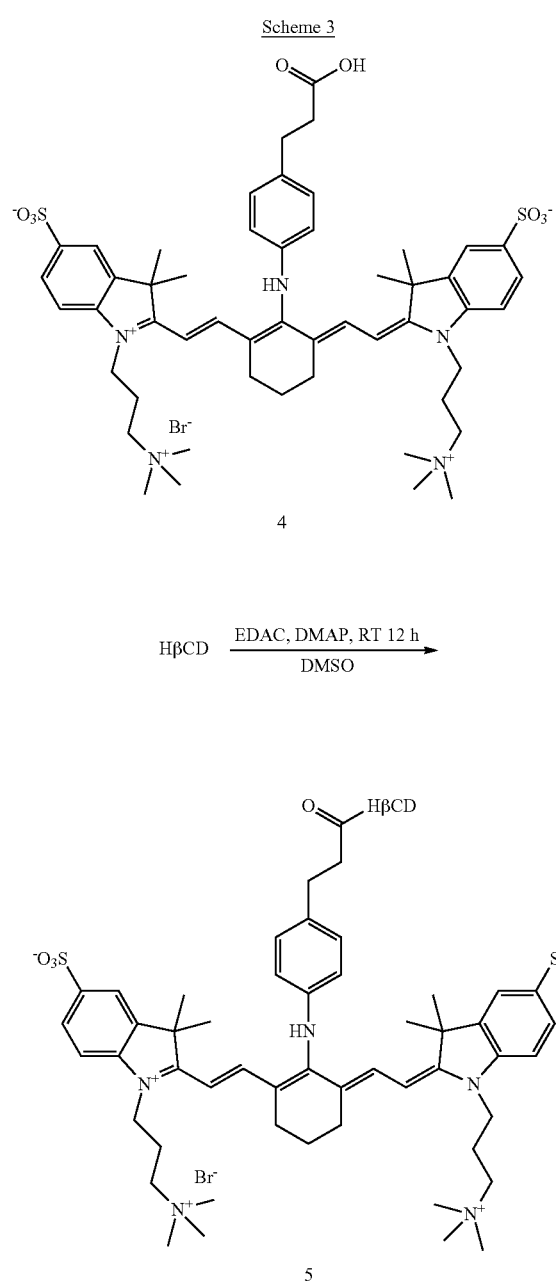

A mixture of 3 (220 mg, 0.27 mmol) and 3-(4-aminophenyl)propanoic acid (178 mg, 1.08 mmol) in DMSO was heated at 65° C. overnight. The reaction mixture was cooled to room temperature and precipitated in dichloromethane. The crude product was purified by RP C18 chromatography to yield a blue solid 130 mg.

FW for $C_{51}H_{68}N_5O_8S_2Br$: 1023.15; exact mass of cation 942.45.

d) Preparation of ABZWCY-HβCD (5).

Materials: 2-hydroxypropyl-β-cyclodextrin (HβCD) was purchased from Sigma-Aldrich (Product No. H-107 of molecular formula $(C_6H_9O_5)_7(C_3H_7O)_{4.5}$; average molecular weight; 1396 (anhyd.) water solubility 45 g/100 mL).

The reaction was carried out according to Scheme 4.

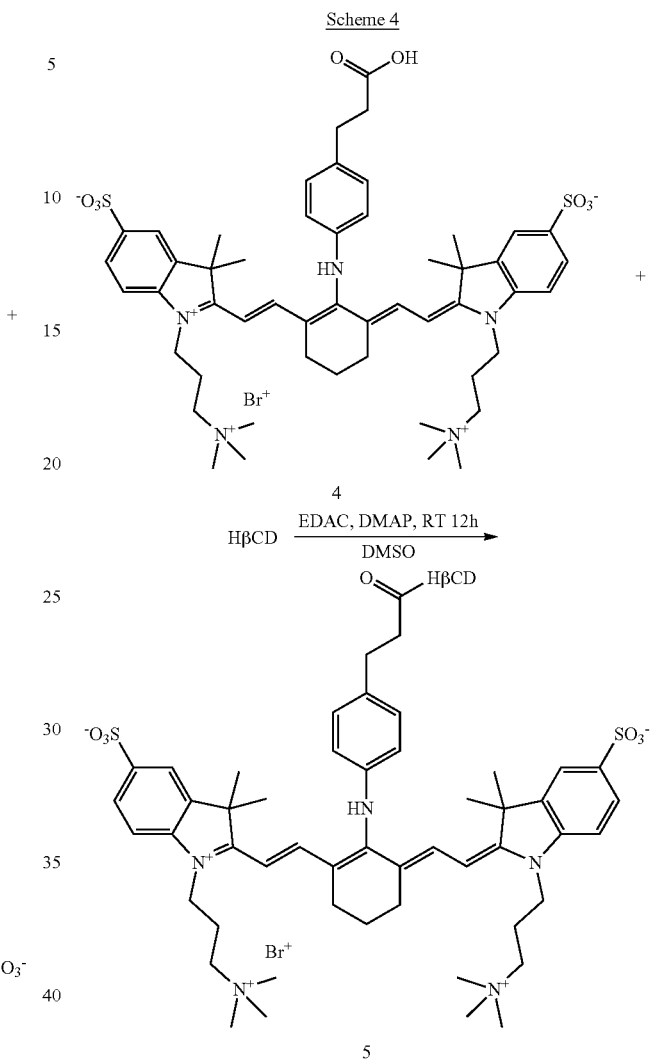

A mixture of dye 4 (40 mg), 1-ethyl-3-(3-dimethylaminopropyl) carbodiimide (20 mg), 4-dimethylaminopyridine (10 mg) and (2-hydroxypropyl)-β-cyclodextrin (550 mg) and DMSO (6 mL) was stirred under room temperature for 12 hours. The reaction mixture was then precipitated in dichloromethane. The obtained crude product was further purified by Sephadex G-10 gel filtration to yield blue solid (5), 350 mg.

MS (ESI) m/z=cluster of peaks between 2200-2470, average 2335; estimated average m/z for ABZWCY-HβCD: 2338 (943 (ABZWCY)+1396 (HβCD, as indicated by producer).

Figure 3:
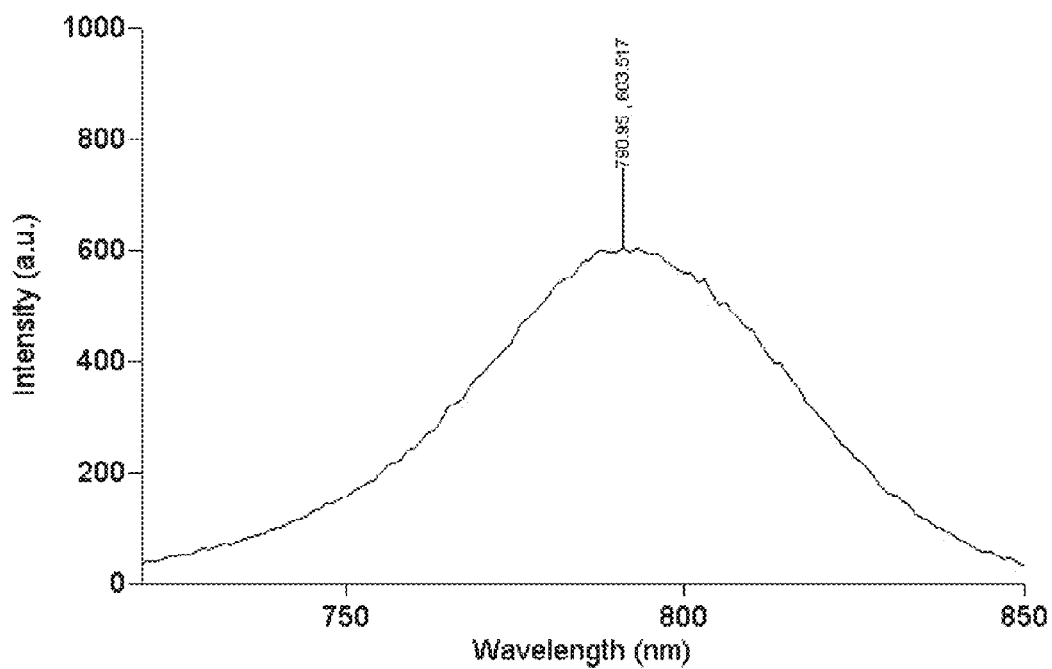
FIG. 3: Emission spectrum of ABZWCY-HβCD in methanol.
Figure 4:
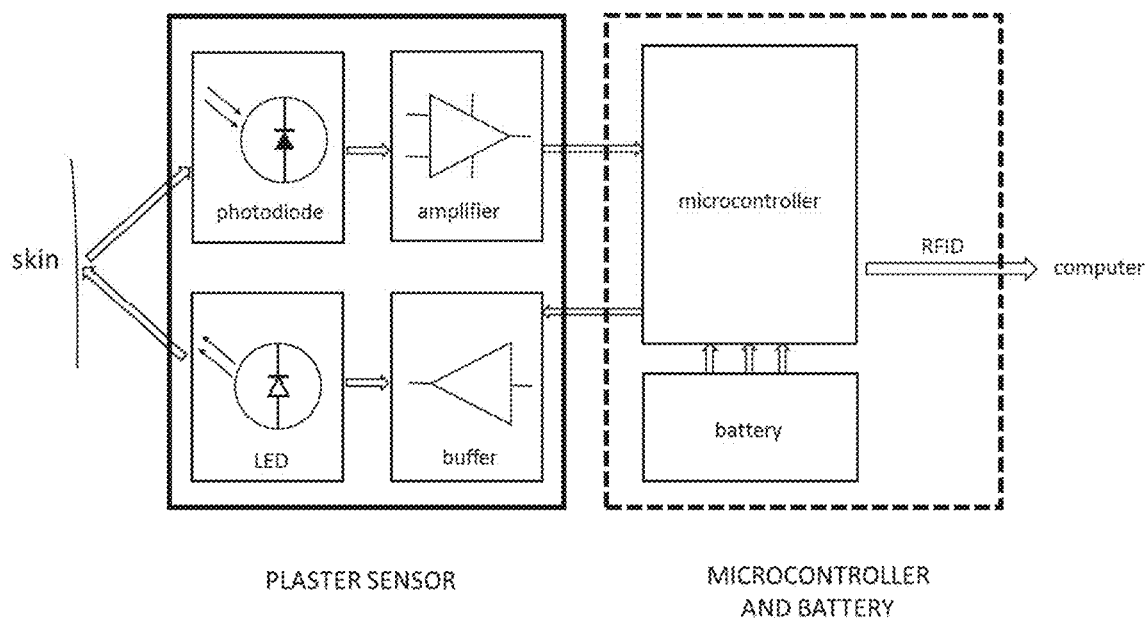
FIG. 4: Schematic diagram of the transcutaneous measuring device.

Absorption max=700 nm; Emission max=791 nm. Absorption and emission spectra are shown in FIGS. 3 and 4.

Water solubility>100 mg/mL.

EXAMPLE 2

Plasma Protein Binding (PPB) for ABZWCY-HβCD

Stock solution preparation. An ABZWCY-HβCD/plasma stock solution was prepared by incubation of 500 μg/ml ABZWCY-HβCD (in PBS solution) with rat plasma protein at 37° C. for 1 hour.

Equilibrium dialysis. Plasma protein binding measurements were performed by equilibrium dialysis technique using a two-chamber dialysis set up. 400 µl of the stock solution (see above) was placed into one side of two-chamber dialysis apparatus, another side was filled with 400 µl distilled water, and the marker-protein solution was dialyzed. At 18 and 36 hours, the concentration of the free marker in the water side and plasma side of the cell was determined by absorption spectroscopy and calculated on the basis of Beer's law.

Calculations:

$$PPB\% = C_{marker\ bound\ to\ plasma}/C_{marker\ dye} \times 100$$

$$PPB\% = (C_P - C_W)/(C_P + C_W) \times 100$$

$$PPB\% = (A_P - A_W)/(A_P + A_W) \times 100$$

wherein
$A_P$ represents the absorbance in the plasma side of the cell after dialysis,
$A_W$ represents the absorbance in water side of the cell after dialysis.

PPB % was calculated to be 8.4% (average of 3 experiments).

EXAMPLE 3

Plasma Clearance Half-Life for ABZWCY-HβCD

Figure 5:
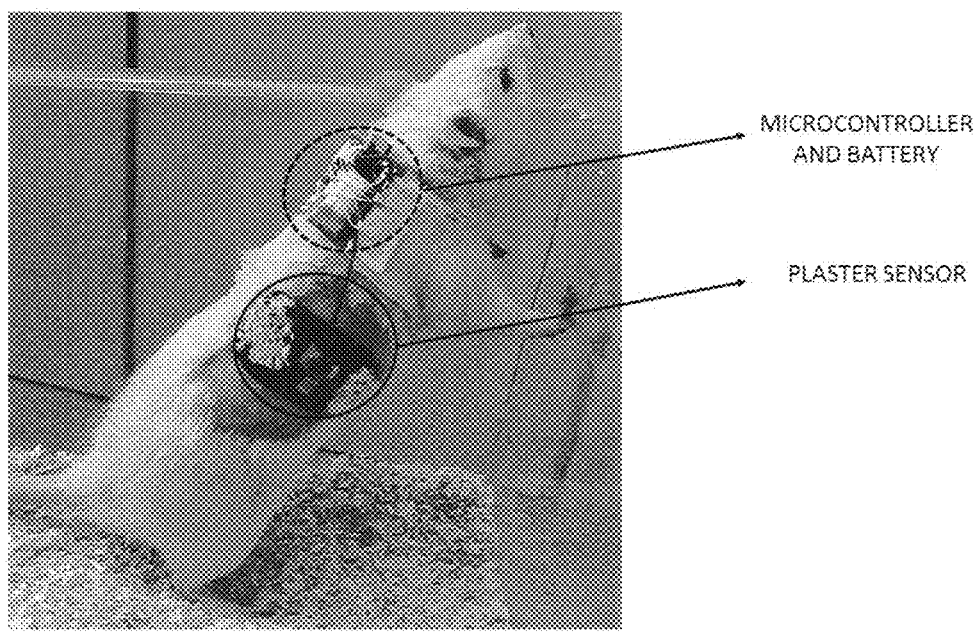
FIG. 5: Application to a rat of the transcutaneous measuring device.

Plasma clearance half-life was analysed in combination with an electronic near infrared device for the transcutaneous fluorescence detection in rat models.
Animal: female Sprague-Dawley rats.
Substance: ABZWCY-HβCD
Dosage: ABZWCY-HβCD: 5 mg/100 g body weight
Electronic near infrared device for transcutaneous fluorescence detection. This device (sensor plaster), described in detail in US2011230739A1, "Transcutaneous Organ Function Measurement", consists of (a) a plaster which can be stuck onto the skin surface; (b) a near infrared emitting diode; (c) a radiation detector. The adhesive surface of the sensor plaster laterally encloses the detector to prevent ambient light from being able to pass to the detector. The near infrared radiation (peak at about 680 nm) is partially absorbed by the marker; the response radiation is detected at about 800 nm. The sensor plaster is electrically connected to an electronic device comprising a microcontroller and a battery, for data acquisition and their RFID transmission to an external computer (FIGS. 5 and 6).

Procedure. SD rats are anesthetized with isoflurane, shaved on the back, then the electronic near infrared device is attached. ABZWCY-HβCD is administered (5 mg/100 g, body weight) via intravenous injection. Transcutaneous measurement usually last 2 h.

Stock solution preparation. An ABZWCY-HβCD/plasma stock solution is prepared by incubation of 500 µg/ml ABZWCY-HβCD (in PBS solution) with rat plasma protein at 37° C. for 1 hour.

Figure 6:
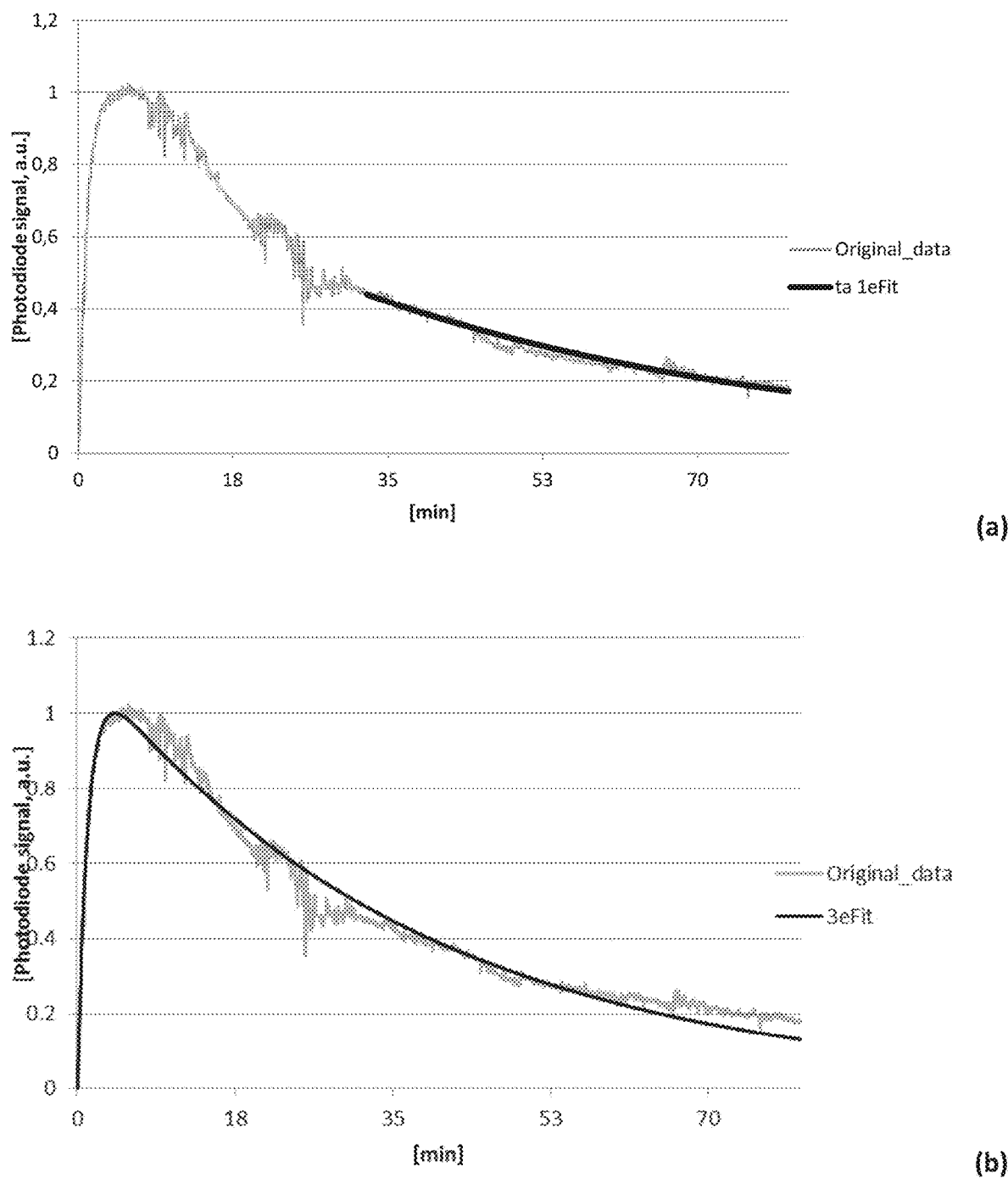
FIG. 6: Plasma clearance kinetics of ABZWCY-HβCD: (a) 1 exponential fitting (1e); 3 exponential fitting (3e).

Plasma clearance kinetics for ABZWCY-HβCD is shown in FIG. 6: (a) 1 exponential fitting (1e); (b) 3 exponential fitting (3e).

EXAMPLE 4

Plasma Clearance Half-Life for ABZWCY-βCD in the Presence of Probenecid

In order to determine whether kidney tubular secretion had any effect on the clearance of these markers, separate pharmacokinetic experiments involving blockage of tubular secretion using Probenecid [p-(dipropyl-sulfamoyl)benzoic acid] were carried out.

The experimental protocol was approved and conducted in accordance with the German Ministry of Health and according to the *The National Animal Protection Guidelines*.
Animal: female Sprague-Dawley rats.
Substances: ABZWCY-HβCD.
Dosage: ABZWCY-HβCD: 5 mg/100 g body weight; Probenecid: 50 mg/kg body weight.

Electronic near infrared device for transcutaneous fluorescence detection. As described above.

Procedure: SD rats are anesthetized with isoflurane, shaved on the back, then the electronic near infrared detector device is attached. ABZWCY-HβCD is administered (5 mg/100 g, body weight) via intravenous injection. Rats are previously treated (30 min. before measurement) with Probenecid (50 mg/kg body weight in 0.9% Saline, intraperitoneally). The transcutaneous measurement lasts approximately 2 h.

Figure 7:
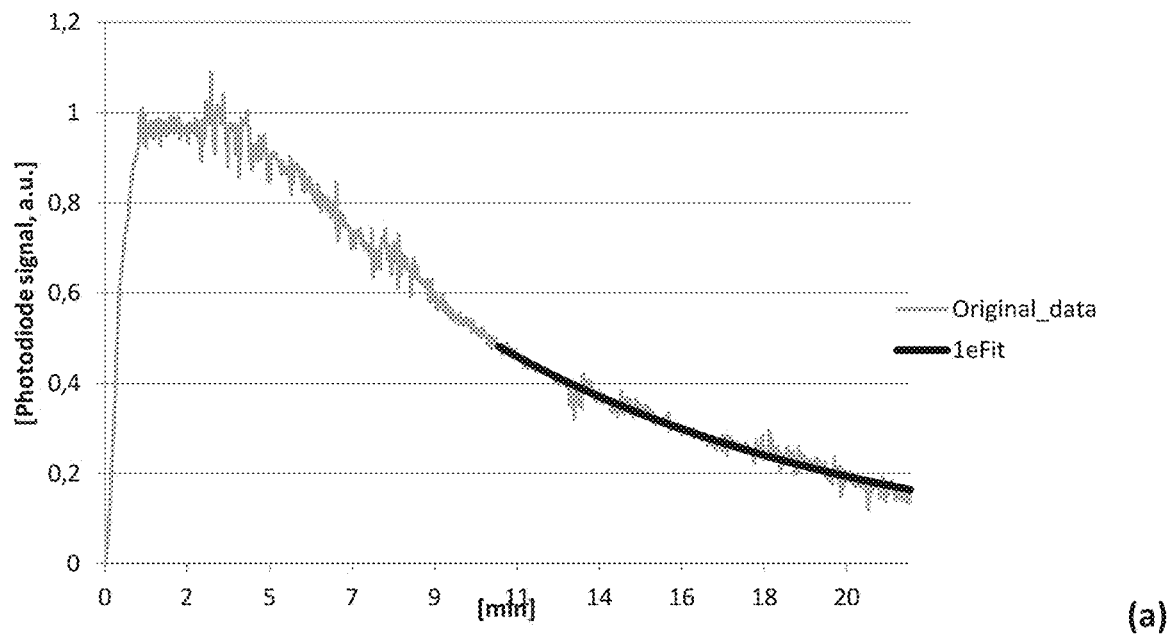
FIG. 7: Plasma clearance kinetics of ABZWCY-HβCD in the presence of Probenecid: (a) 1 exponential fitting (1e); 3 exponential fitting (3e).
Figure 7:
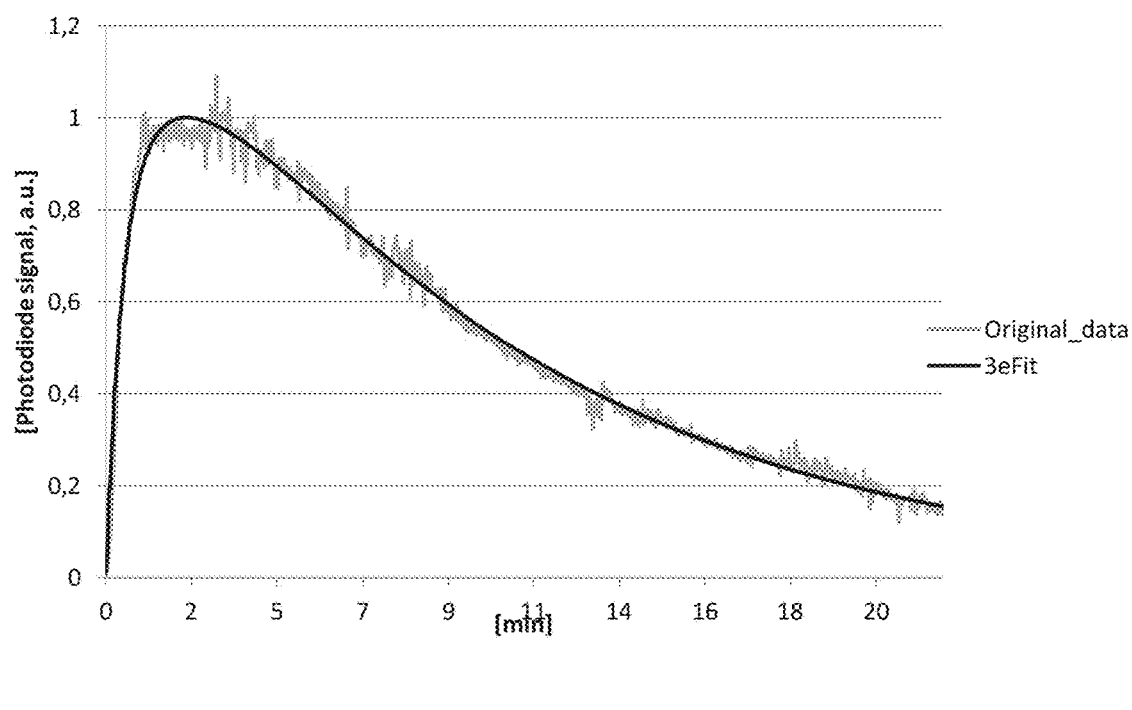

Plasma clearance kinetics for ABZWCY-HβCD in the presence of Probenecid is shown in FIG. 7: (a) 1 exponential fitting (1e); (b) 3 exponential fitting (3e).

Plasma clearance half-life values measured in Examples 3 and 4 are summarized in Table 2.

TABLE 2

| Conjugate | Clearance half-life (minutes) Mean ± SD | |
|---|---|---|
| | 1-parameter fitting | 3-parameter fitting |
| ABZWCY-HβCD (n = 6) | 17.7 ± 3.3 | 16.9 ± 4.7 |
| ABZWCY-HβCD + Probenecid (n = 5) | 18.5 ± 6.6 | 15.9 ± 5.5 |

The invention claimed is:

1. A method for diagnosing kidney function of a mammal, comprising:
(a) administering to the mammal at least one fluorescent compound of formula (I)

$$F-L_n-CD_n \quad (I)$$

wherein
F is a tricarbocyanine residue of formula (II)

$R_1$ and $R_2$ are independently selected from H, $SO_3H$, $CO_2H$, $SO_2NH_2$, $CH_2COOH$, $NH_2$, $NHCOCH_2I$, $NO_2$, Br, Cl, $CH_3$;
$R_3$ and $R_4$ are independently selected from $C_{1-4}$ alkyl, $(CH_2)_3C\equiv CH$, $(CH_2)_4C\equiv CH$ $(CH_2)_5COOH$, $(CH_2)_3SO_3H$, $(CH_2)_4SO_3H$, $(CH_2)_3NH_2$, $(CH_2)_4NH_2$, $(CH_2)_3N^+(CH_3)_3$, $(CH_2)_5N^+(CH_3)_3$, $(CH_2)_3N_3$, $(CH_2)_4N_3$, $(CH_2)_3NHCOCH_2I$, $(CH_2)_4NHCOCH_2I$; $(CH_2CH_2O)_2CH_3$, $(CH_2CH_2O)_3CH_3$, $(CH_2CH_2O)_4CH_3$;

$R_5$, is selected from

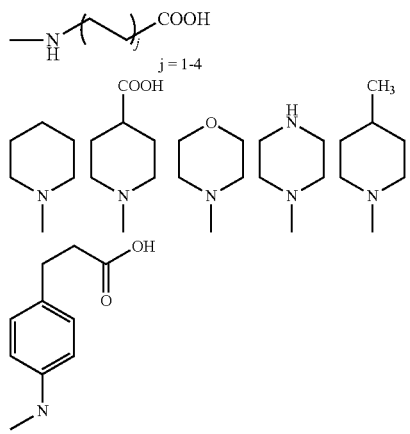

CD is a cyclodextrin residue of formula (III)

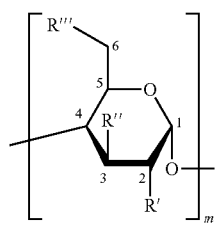

m is and integer equal to 6, 7 or 8,
R', R", R'" are independently selected from OH, OCH$_3$, OCH$_2$CH$_3$, OCH$_2$CHOHCH$_3$, OCHOHCH$_3$, OCH$_2$COOH, O(CH$_2$)$_4$SO$_3$H, N$_3$, NH$_2$, NHCOCH$_3$, OCH$_2$C≡CH, SH;
L is a linker group resulting from the coupling of the tricarbocyanine of formula (II) to the cyclodextrin(s) of formula (III) according to the following Table:

| Functional group of the tricarbocyanine (F) in any of the groups $R_3$, $R_4$ or $R_5$ | Functional group of the cyclodextrin (CD) in any of the groups R', R" or R'" | Linker group (L) |
| --- | --- | --- |
| COOH | OH | —C(O)O— |
| COOH | NH$_2$ | —C(O)NH— |
| NH$_2$ | COOH | —NHC(O)— |
| NHCOCH$_2$I | SH | NHC(O)CH$_2$S— |
| C≡CH | N$_3$ | triazole linker |
| N$_3$ | C≡CH | triazole linker | n is an integer from 1 to 4,
and salts thereof, and
(b) detecting and measuring the fluorescence emission of the at least one fluorescent compound.

2. The method according to claim 1, wherein the administration is intravenous.

3. The method according to claim 1, wherein the fluorescence detection and measurement comprise the detection and measurement of fluorescence emerging from the mammalian skin in response to excitation with a red light or near infrared light source.

4. The method according to claim 1, wherein the fluorescence is detected and measured by placing a sensor device onto the mammalian skin.

5. The method according to claim 1, wherein the method is carried out over a clinically relevant measuring time.

6. The method according to claim 1, wherein m is equal to 7 or 8.

7. The method according to claim 1, wherein at least one of the R', R", R'" groups is selected from OCH$_3$, OCH$_2$CH$_3$, OCH$_2$CHOHCH$_3$, with the provision that at least one group from R', R", R'" is OH.

8. The method according to claim 1, wherein R' and R" are OH, and R'" is selected from OCH$_3$, OCH$_2$CH$_3$, OCH$_2$CHOHCH$_3$, and wherein the substitution degree of R'" is comprised between 0.5 and 1.5 for each unit of Formula (III).

9. The method according to claim 1, wherein R' and R" are OH, and R'" is OCH$_2$CHOHCH$_3$, and wherein the substitution degree of R'" is comprised between 0.5 and 1.5 for each unit of Formula (III).

10. The method according to claim 1, wherein $R_1$ and $R_2$ are independently selected from H, SO$_3$H and COOH.

11. The method according to claim 1, wherein $R_3$ and $R_4$ are independently selected from methyl, ethyl, (CH$_2$)$_5$COOH, (CH$_2$)$_4$SO$_3$H, (CH$_2$)$_3$N$^+$(CH$_3$)$_3$.

12. The method according to claim 1, wherein L is selected from an ester, an ether, and an amide.

13. The method according to claim 1, wherein the fluorescent compound of formula (I) is selected from:
a compound of formula (IV):

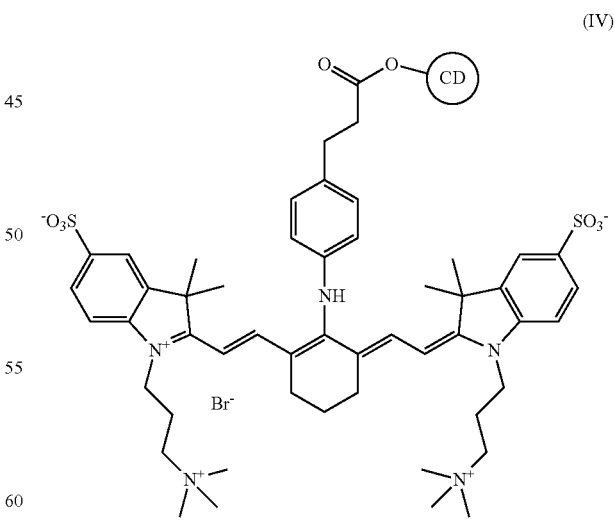

wherein CD is 2-hydroxypropyl-β-cyclodextrin (HβCD) or 2-hydroxypropyl-γ-cyclodextrin (HγCD) and the linker L of formula (I) is an ester bond formed in the coupling reaction of the carboxyl group of the tricarbocyanine with a residue group R'"=OH of CD;

a compound of formula (V):

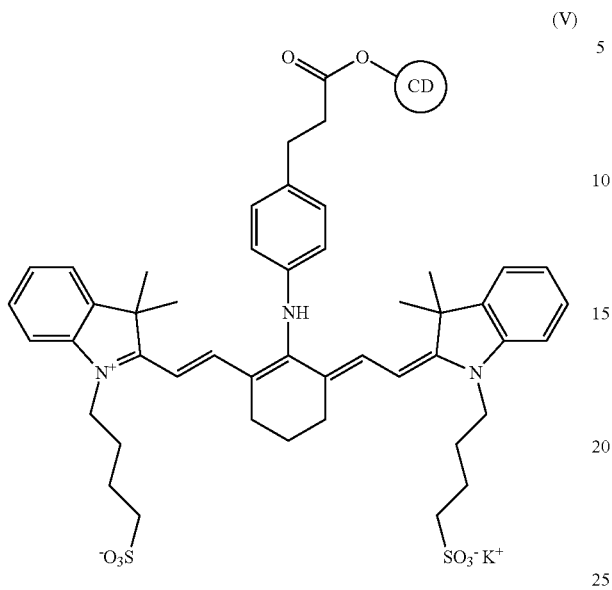

wherein CD is 2-hydroxypropyl-β-cyclodextrin (HβCD) or 2-hydroxypropyl-γ-cyclodextrin (HγCD) and the linker L of formula (I) is an ester bond formed in the coupling reaction of the carboxyl group of the tricarbocyanine with a residue group R'''=OH of CD;

a compound of formula (IX):

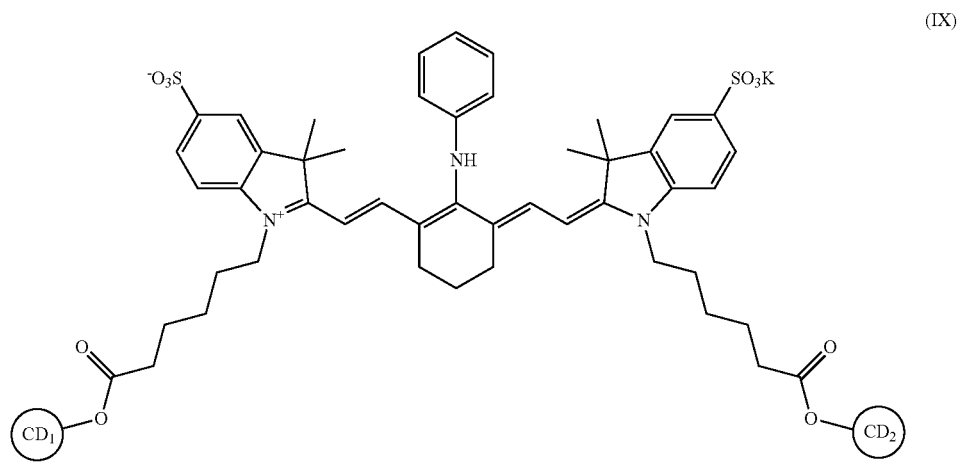

wherein $CD_1$ and $CD_2$ are, independently, 2-hydroxypropyl-β-cyclodextrin (HβCD) or 2-hydroxypropyl-γ-cyclodextrin (HγCD) and the linkers L of formula (I) are ester bonds formed in the coupling reaction of a carboxyl group of the tricarbocyanine with a residue group R'''=OH of $CD_1$ and $CD_2$, respectively;

a compound of formula (XI):

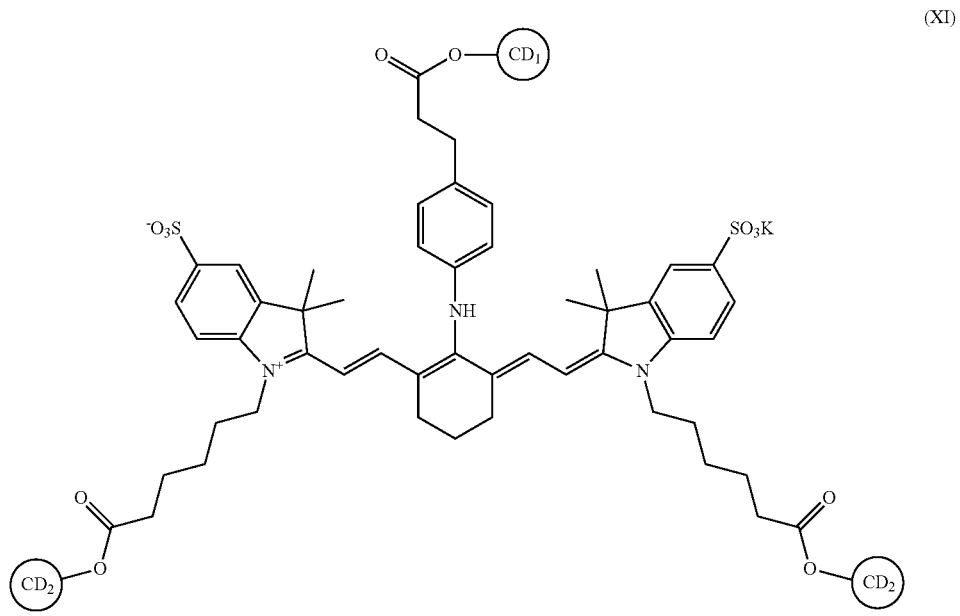

(XI)

wherein $CD_1$, $CD_2$ and $CD_3$ are, independently, 2-hydroxypropyl-β-cyclodextrin (HβCD) or 2-hydroxypropyl-γ-cyclodextrin (HγCD) and the linkers L of formula (I) are ester bonds formed in the coupling reaction of a carboxyl group of the tricarbocyanine with a residue group R'''=OH of $CD_1$, $CD_2$ and $CD_3$, respectively.

a compound of formula (XII):

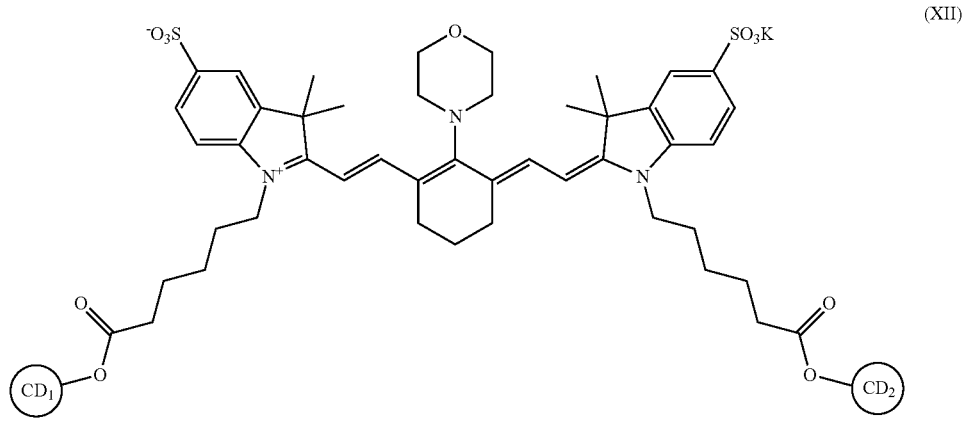

(XII)

wherein $CD_1$ and $CD_2$ are, independently, 2-hydroxypropyl-β-cyclodextrin (HβCD) or 2-hydroxypropyl-γ-cyclodextrin (HγCD) and the linkers L of formula (I) are ester bonds formed in the coupling reaction of a carboxyl group of the tricarbocyanine with a residue group R'''=OH of $CD_1$ and $CD_2$, respectively.

* * * * *